United States Patent
Larsen et al.

(10) Patent No.: US 11,400,154 B2
(45) Date of Patent: *Aug. 2, 2022

(54) METHOD OF TREATING A LOCALIZED FIBROTIC DISORDER USING AN IL-33 ANTAGONIST

(71) Applicant: 180 Therapeutics LP, Cambridge, MA (US)

(72) Inventors: Glenn Larsen, Sudbury, MA (US); Jagdeep Nanchahal, Headington (GB); Marc Feldmann, London (GB)

(73) Assignee: 180 THERAPEUTICS LP, Cambridge, MA (US)

( * ) Notice: Subject to any disclaimer, the term of this patent is extended or adjusted under 35 U.S.C. 154(b) by 137 days.

This patent is subject to a terminal disclaimer.

(21) Appl. No.: 16/707,631

(22) Filed: Dec. 9, 2019

(65) Prior Publication Data

US 2020/0338193 A1    Oct. 29, 2020

Related U.S. Application Data

(63) Continuation of application No. 15/555,027, filed as application No. PCT/US2016/020101 on Feb. 29, 2016, now Pat. No. 10,500,273.

(60) Provisional application No. 62/127,157, filed on Mar. 2, 2015.

(51) Int. Cl.

| | |
|---|---|
| A61K 39/395 | (2006.01) |
| C07K 16/24 | (2006.01) |
| A61K 38/19 | (2006.01) |
| A61P 43/00 | (2006.01) |
| C07K 16/28 | (2006.01) |
| A61K 31/00 | (2006.01) |
| A61K 9/00 | (2006.01) |
| A61K 31/713 | (2006.01) |
| A61K 45/06 | (2006.01) |
| C12N 15/113 | (2010.01) |
| A61K 39/00 | (2006.01) |

(52) U.S. Cl.
CPC .......... *A61K 39/395* (2013.01); *A61K 9/0019* (2013.01); *A61K 9/0053* (2013.01); *A61K 31/00* (2013.01); *A61K 31/713* (2013.01); *A61K 38/193* (2013.01); *A61K 39/3955* (2013.01); *A61K 45/06* (2013.01); *A61P 43/00* (2018.01); *C07K 16/241* (2013.01); *C07K 16/244* (2013.01); *C07K 16/2863* (2013.01); *C07K 16/2878* (2013.01); *C12N 15/1136* (2013.01); *A61K 9/00* (2013.01); *A61K 2039/505* (2013.01); *A61K 2039/507* (2013.01); *A61K 2039/54* (2013.01); *A61K 2039/545* (2013.01); *C07K 2317/21* (2013.01); *C07K 2317/24* (2013.01); *C07K 2317/31* (2013.01); *C07K 2317/52* (2013.01); *C07K 2317/55* (2013.01); *C07K 2317/622* (2013.01); *C07K 2317/76* (2013.01); *C07K 2319/30* (2013.01); *C12N 2310/14* (2013.01); *C12N 2310/531* (2013.01); *C12N 2320/31* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 7,431,927 B2 | 10/2008 | Couto et al. | |
| 8,034,347 B2 | 10/2011 | Hempstead et al. | |
| 9,138,458 B2 | 9/2015 | Nanchahal et al. | |
| 10,500,273 B2 | 12/2019 | Larsen et al. | |
| 2001/0021380 A1 | 9/2001 | Pluenneke | |
| 2003/0176332 A1 | 9/2003 | Olmarker et al. | |
| 2005/0032183 A1 | 2/2005 | Oss et al. | |
| 2005/0175665 A1 | 8/2005 | Hunter et al. | |
| 2006/0246115 A1 | 11/2006 | Rueda et al. | |
| 2009/0226500 A1 | 9/2009 | Avelar | |
| 2009/0304699 A1 | 12/2009 | Amatucci et al. | |
| 2011/0130710 A1 | 6/2011 | Becker et al. | |
| 2012/0094934 A1 | 4/2012 | Collard et al. | |
| 2012/0207752 A1 | 8/2012 | Chackerian et al. | |
| 2013/0287760 A1 | 10/2013 | Nanchahal et al. | |
| 2013/0310404 A1 | 11/2013 | Saragovi et al. | |
| 2013/0336980 A1 | 12/2013 | Duffy et al. | |
| 2014/0212412 A1 | 7/2014 | Rankin | |
| 2014/0271642 A1 | 9/2014 | Murphy et al. | |

(Continued)

FOREIGN PATENT DOCUMENTS

| | | |
|---|---|---|
| EP | 1 725 261 | 1/2011 |
| WO | WO 1994-09137 | 4/1994 |

(Continued)

OTHER PUBLICATIONS

Smith et al, Journal of Shoulder and Elbow Surgery 10: 149-151, 2001.*

(Continued)

*Primary Examiner* — Bridget E Bunner
*Assistant Examiner* — Fozia M Hamud
(74) *Attorney, Agent, or Firm* — John P. White

(57) ABSTRACT

The subject invention provides a method of treating a patient suffering from a localized fibrotic condition which comprises administering to the patient an amount of an IL-33 antagonist effective to treat the patient. The subject invention also provides a method of treating a patient suffering from a localized fibrotic condition which comprises administering to the patient an amount of a TNF receptor 2 (TNFR2) antagonist effective to treat the patient.

18 Claims, 35 Drawing Sheets
Specification includes a Sequence Listing.

(56) References Cited

U.S. PATENT DOCUMENTS

| | | |
|---|---|---|
| 2016/0280775 A1 | 9/2016 | Nanchahal et al. |
| 2018/0036404 A1 | 2/2018 | Larsen et al. |
| 2019/0202907 A1 | 7/2019 | Nanchahal et al. |
| 2019/0225682 A1 | 7/2019 | Nanchahal et al. |

FOREIGN PATENT DOCUMENTS

| | | |
|---|---|---|
| WO | WO 99-59632 | 11/1999 |
| WO | WO 2000/043031 | 7/2000 |
| WO | WO 2000-064479 | 11/2000 |
| WO | WO 2005/076999 | 8/2005 |
| WO | WO 2007/060411 | 5/2007 |
| WO | WO 2008/132709 | 11/2008 |
| WO | WO 2008/144610 | 11/2008 |
| WO | WO 2010/087972 | 8/2010 |
| WO | WO 2013/165894 | 11/2013 |
| WO | WO 2014/164959 | 10/2014 |
| WO | WO 2014/174517 A1 | 10/2014 |
| WO | WO 2015/006469 A2 | 1/2015 |
| WO | WO 2016/187068 A1 | 11/2016 |
| WO | WO 2018/045210 | 3/2018 |
| WO | WO 2018/045213 | 3/2018 |

OTHER PUBLICATIONS

Tamai, Journal of Orthopaedic Science, 2014, vol. 19, pp. 1-5.*

Apr. 14, 2017 Response to Oct. 14, 2016 Office Action issued in connection with U.S. Appl. No. 14/852,442.

Apr. 20, 2015 Response to Dec. 19, 2014 Office Action issued in connection with U.S. Appl. No. 13/882,262.

Aug. 21, 2018 response to Feb. 21, 2018 Office Action issued in connection with U.S. Appl. No. 14/852,442.

Aug. 4, 2014 Office Action issued in connection with U.S. Appl. No. 13/882,262.

Brown, Julia "Endometriosis: an overview of Cochrane Reviews." (abstract) Published Mar. 2014 by the Editorial Group: Cochran Menstrual Disorders and Subfertility Group.

Catherine Ball et al., "Optimal functional outcome measures for assessing treatment for Dupuytren's disease: a systematic review and recommendations for future practice", BMC Musculoskeletal Disorders, vol. 14, No. 1, p. 131, Apr. 10, 2013.

Dec. 19, 2014 Office Action issued in connection with U.S. Appl. No. 13/882,262.

Dec. 4, 2014 Response to Aug. 4, 2014 Office Action issued, in connection with U.S. Appl. No. 13/882,262.

Feb. 21, 2018 Office Action issued in connection with U.S. Appl. No. 14/852,442.

Guo et al. "Contributions of angiotensin II and tumor necrosis factor-a to the development of renal fibrosis", Am J Physiol Renal Physiol, vo. 280, May 1, 2001 (May 1, 2001), pp. F777-F785, XP055506483.

International Search Report issued in connection with PCT International Application No. PCT/US2016/020101, dated May 2016.

International Search Report mailed by the International Searching Authority (ISA/US) dated Feb. 6, 2012 in connection with PCT International Application No. PCT/EP2011/069147.

Jan. 25, 2018 Response to Jul. 25, 2017 Office Action issued in connection with U.S. Appl. No. 14/852,442.

Jan. 28, 2019 Response to Jun. 28, 2018 Extended European Search Report issued in connection with European Patent Application No. 16759325.0.

Jul. 25, 2017 Office Action issued in connection with U.S. Appl. No. 14/852,442.

Jun. 28, 2018 Extended European Search Report issued in connection with European Patent Application No. 16759325.

Koninckx et al. "Anti-TNF-a treatment tor deep endometriosis-associated pain: a randomized placebo-controlled trial" Human Reproduction vol. 23, No. 9 pp. 2017-2023, 2008.

Kurukahvecioglu et al. Infliximab "TNF-alpha antagonist" decreases intraabdominal adhesions. Saudi Med J 2007; vol. 28(12):1830-1835.

Lu, D, et al. "Anti-TNF-α treatment for pelvic pain associated with endometriosis." Cochrane Database Syst Rev. Mar. 28, 2013, 10.1002/14651858.CD008088.pub3.

Munoz-Hernando "Endometriosis: alternative methods of medical treatment", International Journal of Women's Health 2015:7.

Notice of allowance issued in connection with U.S. Appl. No. 14/852,442, dated Dec. 2018.

Oct. 14, 2016 Office Action issued in connection with U.S. Appl. No. 14/852,442.

Quaoyan Gao et al. "The potential role of IL-33/ST2 signaling in fibrotic diseases", Journal of Leukocyte Biology, vol. 98, No. 1, pp. 15-22, Apr. 16, 2015.

Rankin, Andrew, et al. "IL-33 induces IL-13-Dependent Cutaneous Fibrosis." The Journal of Immunology, The American Association of Immunologists, vol. 184, No. 3, pp. 1526-1535, Feb. 1, 2010.

Schydlowsky et al. "Treatment of Frozen Shoulder with Subcutaneous TNF-alpha blockade compared with local glucocorticoid injection: a random pilot study." Clin Rheumatol 2012.

Sep. 20, 2018 Extended European Search Report issued in connection with European Patent Application No. 16759326.8.

Tamar McHedlidze et al. "Interleukin-33-Dependent Innate Lymphoid Cells Mediate Hepatic Fibrosis", Immunity, vol. 39, No. 2, pp. 357-371, Aug. 1, 2013.

Verjee et al. "Unraveling the signaling pathway promoting Fibrosis in Dupuytren's disease reveals TNF as a therapeutic target", Proceedings of the National Academy of Sciences, vol. 110, No. 10, Feb. 19, 2013 (Feb. 19, 2013), pp. E928-E928, XP055506364.

Written Opinion of the International Searching Authority issued by the International Searching Authority (ISA/US) dated Apr. 30, 2013 in connection with PCT International Application No. PCT/EP2011/069147.

Written Opinion of the International Searching Authority issued in connection with PCT International Application No. PCT/US2016/020101, dated May 2016.

Yang, et al., "A variant of TNFR2-Fc fusion protein exhibits improved efficacy in treating experimental rheumatoid arthritis", PLoS Computational Bioloay, Feb. 5, 2010, vol. 6, Iss. 2, pp. 1-7.

* cited by examiner i ii iii i ii

α-SMA in NPFD and PFD treated with TNF

COL1A1 in NPFD and PFD treated with TNF

α- SMA in NPFD and PFD treated with TNF

ST2 and IL-33 in NPFD and PFD treated with TNF

SEQUENCE LISTING

```
<160> NUMBER OF SEQ ID NOS: 3

<210> SEQ ID NO 1
<211> LENGTH: 21
<212> TYPE: DNA
<213> ORGANISM: Homo sapiens

<400> SEQUENCE: 1
gccuuggguc uacuaauaat t                                             21

<210> SEQ ID NO 2
<211> LENGTH: 21
<212> TYPE: DNA
<213> ORGANISM: Homo sapiens
```

```
<400> SEQUENCE: 2
cggugacugu cccaacuuut t                                              21

<210> SEQ ID NO 3
<211> LENGTH: 21
<212> TYPE: DNA
<213> ORGANISM: Homo sapiens

<400> SEQUENCE: 3
guuacaccgu ggauugguat t                                              21
```

METHOD OF TREATING A LOCALIZED FIBROTIC DISORDER USING AN IL-33 ANTAGONIST

CROSS-REFERENCE TO RELATED APPLICATIONS

This Application is a continuation of U.S. patent application Ser. No. 15/555,027, filed Dec. 15, 2017, now U.S. Pat. No. 10,500,273 issued Dec. 10, 2019, which claims benefit from U.S. Provisional Application No. 62/127,157, filed Mar. 2, 2015, the entire contents of each of which are hereby incorporated by reference herein.

REFERENCE TO A SEQUENCE LISTING

This application incorporates by reference nucleotide and/or amino acid sequences which are present in the file named "191209_87158-AA-PCT-US_Substitute_Sequence_ Listing_CAS.txt", which is 864 bytes in size, and which was created Dec. 9, 2019 in the IBM-PC machine format, having an operating system compatibility with MS-Windows, which is contained in the text file filed Dec. 9, 2019 as part of this application.

Throughout this application various publications are referenced, most typically by the last name of the first author and the year of publication. Full citations for these publications are set forth in a section entitled References immediately preceding the claims. The disclosures of these publications in their entireties are hereby incorporated by reference into this application in order to more fully describe the state of the art to which the invention relates.

BACKGROUND OF INVENTION

Dupuytren's Disease

Dupuytren's disease, also known as palmar fibromatosis or in its established disease stage Dupuytren's contracture, is a disease associated with the buildup of extracellular matrix materials such as collagen on the connective tissue of the hand (the palmar fascia) causing it to thicken and shorten with the result that the fingers curl into the palm.

Dupuytren's disease is a common fibrotic disorder (Hindocha, 2009). The mean age of treatment for the disease is 63 years (Chen, 2011), with onset approximately 10 years earlier. It exhibits a strong hereditary basis (Hurst, 2009). Dupuytren's disease causes the fingers to curl irreversibly into the palm, leading to significant impairment of hand function.

There is no approved treatment for early disease. Once patients have established deformities, the mainstay of treatment is surgical excision (fasciectomy) of the diseased tissue or cords (Davis, 2013). Patients with advanced disease are treated by surgical excision of diseased tissues. Surgery is recommended when patients develop flexion deformities of the digits of 30 degrees or more of the finger joints and suffer impaired hand function (Rayan, 2007). Between 10-12% of patients develop recurrence over 3 years following surgery (Ullah, 2009; van Rijssen, 2012) and are treated with more extensive surgery that involves excision of the diseased tissue and the overlying skin (dermofasciectomy). Postoperatively, patients require 3-6 months of hand therapy and splintage (Hughes, 2003; Larson, 2008). Complications occur in about 20% of surgical patients (Bulstrode, 2005; Crean, 2011).

Alternative, less invasive techniques have been developed to disrupt the cords of diseased tissue with either a needle (Beaudreuil, 2012) or collagenase digestion (Hurst, 2009). However, recurrence rates are high, affecting 70% of patients treated with percutaneous needle fasciotomy (van Rijssen, 2012) and 35% of those treated with collagenase (Peimer, 2013) at 3 years. The complication rate is 20% following needle fasciotomy (Crean, 2011) and over 70% after collagenase injection (Hurst, 2009).

In the United Kingdom, the vast majority of patients with established disease and finger contractures are treated surgically (Davis, 2013). Over 90% of the 12,900 patients who have surgery for Dupuytren's disease per annum in the United Kingdom undergo fasciectomy. Recurrence rates are of the order of 12% within 3 years of fasciectomy and the costs for dermofasciectomy for recurrent disease are much higher (Ullah, 2009). Neither surgical fasciectomyor or collagenase injection was found to be an effective use of health care resources (Chen, 2011).

Intralesional steroid injection and radiotherapy are two additional possible treatments for Dupuytren's disease. Intralesional steroid injection has been proposed based on a retrospective study of 63 patients with early Dupuytren's disease treated with steroid injection into the nodules at 6 week intervals (Ketchum, 2000). However, this treatment has found limited acceptance. Radiotherapy has also been used although 20-30% of patients developed long term adverse effects, including dry skin, increased desquamation, skin atrophy, telangiectasia, erythema, altered heat and pain sensation (Seegenschmiedt, 2001; Pohl, 2002; Betz, 2010). Based on the published data The National Institute for Health and Care Excellence (NICE) does not recommend radiotherapy for Dupuytren's disease (NICE, 2010).

Therefore, there is a need to develop an effective therapy to prevent progression of early Dupuytren's disease while avoiding the necessity for invasive procedures. Also, there is a need to prevent the development of recurrent disease following surgery, needle fasciotomy, or collagenase injection in patients with established finger contractures.

Combination Therapy

The administration of two drugs to treat a given condition, such as a localized fibrotic disorder, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 1999). In one example, combined administration of GA (glatiramer acetate) and interferon (IFN) has been experimentally shown to abrogate the clinical effectiveness of either therapy (Brod 2000). In another experiment, it was reported that the addition of prednisone in combination therapy with IFN-β antagonized its up-regulator effect. Thus, when two drugs are administered to treat the same condition, it is unpredictable whether each will complement, have no effect on, or interfere with, the therapeutic activity of the other in a human subject.

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side profile of each drug. In one example, the combination of natalizumab and interferon β-1a was observed to increase the risk of unanticipated side effects. (Vollmer, 2008; Rudick 2006; Kleinschmidt-DeMasters, 2005; Langer-Gould 2005)

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry, 1999).

Therefore, the state of the art at the time of filing is that the effects of a combination therapy of two drugs, in particular an IL-33 antagonist and a TNF-α antagonist or TNF-α receptor, cannot be predicted until experimental results are available.

SUMMARY OF THE INVENTION

The subject invention provides a method of treating a patient suffering from a localized fibrotic condition which comprises administering to the patient an amount of an IL-33 antagonist effective to treat the patient.

The subject invention also provides a method of treating a patient suffering from liver fibrosis which comprises administering to the patient an amount of an IL-33 antagonist effective to treat the patient.

The subject invention also provides a method of treating a patient suffering from a localized fibrotic condition which comprises administering to the patient an amount of a TNF receptor 2 (TNFR2) antagonist effective to treat the patient.

The invention additionally provides a method of treating a patient suffering from liver fibrosis or lung fibrosis which comprises administering to the patient an amount of a TNFR2 antagonist effective to treat the patient.

BRIEF DESCRIPTION OF THE FIGURES

FIG. 4A: Characterization of cells in Dupuytren's nodules by FACS. The majority of the cells present are myofibroblasts, there are significant numbers of CD45+ immune cells, with macrophages, including classically activated (M1) and alternatively activated (M2) phenotypes, T cells and mast cells.

FIG. 4B: Immunostaining of Dupuytren's nodules. The majority of the cells are α-SMA positive myofibroblasts with interspersed CD68+ macrophages and tryptase positive mast cells.

FIG. 4C: Chemokines secreted by freshly disaggregated cells from Dupuytren's nodules. Chemokine levels were detected by electrochemiluminescence assays in the supernatants of freshly disaggregated Dupuytren's nodular cells after 24 hours. n=40 patient samples. CCL2 and CXCL10 are known chemoattractants for macrophages and CXCL8 (IL-8), CCL26 and CXCL10 for mast cells.

|  | CXCL8 | CCL2 | CCL26 | CXCL10 | CCL17 | CCL3 |
|---|---|---|---|---|---|---|
| Mean | 3376 | 955.0 | 1056 | 238.8 | 57.37 | 57.61 |
| Std. Deviation | 2069 | 993.1 | 375.2 | 115.5 | 33.08 | 46.44 |
| Std. Error of Mean | 354.8 | 167.9 | 73.58 | 21.10 | 6.366 | 9.683 |

|  | CCL11 | CCL4 | CCL13 | CCL22 | CCL8 | SCF |
|---|---|---|---|---|---|---|
| Mean | 45.15 | 49.05 | 34.40 | 25.88 | 6.722 | 10.85 |
| Std. Deviation | 26.64 | 58.88 | 14.39 | 11.56 | 5.592 | 9.004 |
| Std. Error of Mean | 4.638 | 12.85 | 2.628 | 2.313 | 1.318 | 1.592 |

FIGS. 5A-5G: Dupuytren's disease is a localized inflammatory disorder characterized by the secretion of cytokines, including TNF, which leads to increased expression of TNFR2 in palmar fibroblasts and myofibroblasts from patients with Dupuytren's disease.

Figure 5A:
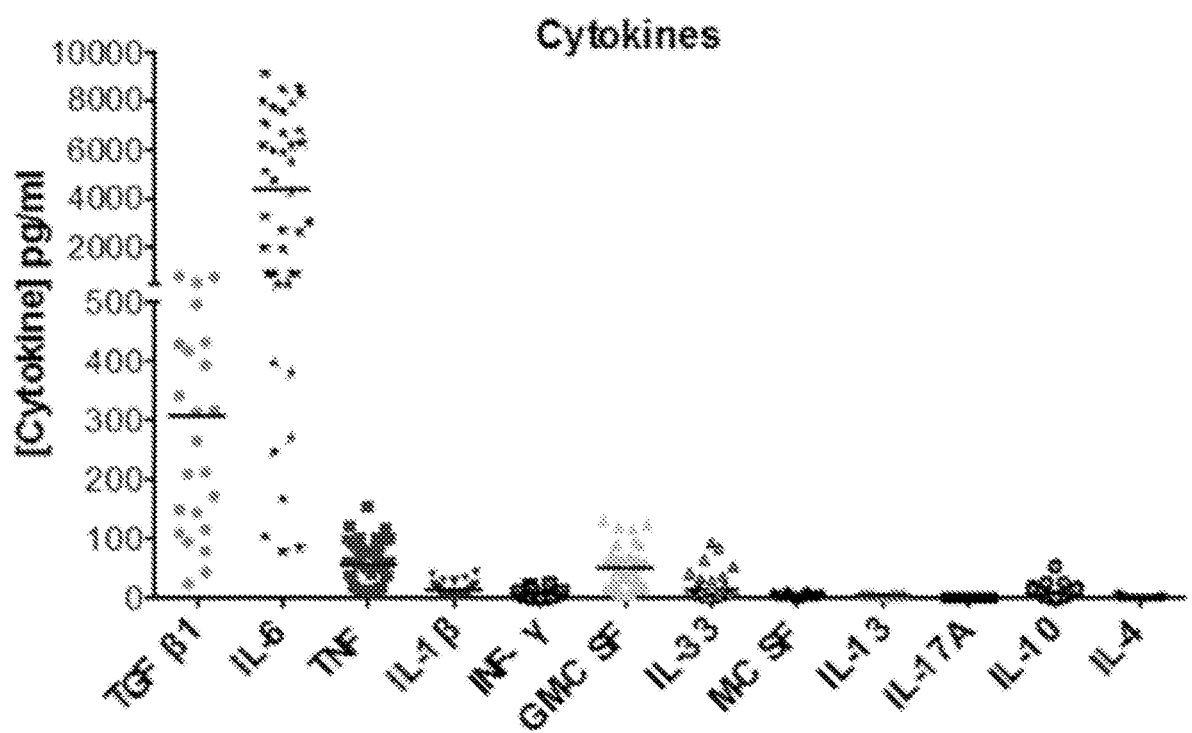

FIG. 5A: A range of cytokines are secreted, including TNF and IL-33. Cytokines released by freshly isolated nodular cells in monolayer culture for 24 hours were measured using electrochemiluminescence. N=20 samples for TGFβ1 and 40 for all other cytokines.

|  | TGF-β1 | IL-6 | TNF | IL-1β | IFN-γ | GM-CSF |
|---|---|---|---|---|---|---|
| Mean | 306.2 | 4333 | 55.75 | 12.11 | 4.786 | 48.79 |
| Std. Deviation | 231.6 | 3465 | 37.49 | 10.17 | 5.424 | 34.58 |
| Std. Error of Mean | 48.28 | 534.7 | 5.784 | 1.570 | 0.8369 | 5.336 |

|  | IL-33 | M-CSF | IL-13 | IL-17A | IL-10 | IL-4 |
|---|---|---|---|---|---|---|
| Mean | 13.59 | 2.617 | 1.915 | 0.08417 | 7.772 | 0.5413 |
| Std. Deviation | 20.70 | 2.496 | 0.6281 | 0.03632 | 9.713 | 1.144 |
| Std. Error of Mean | 2.988 | 0.2942 | 0.07205 | 0.006524 | 1.499 | 0.1832 |

Figure 5B:
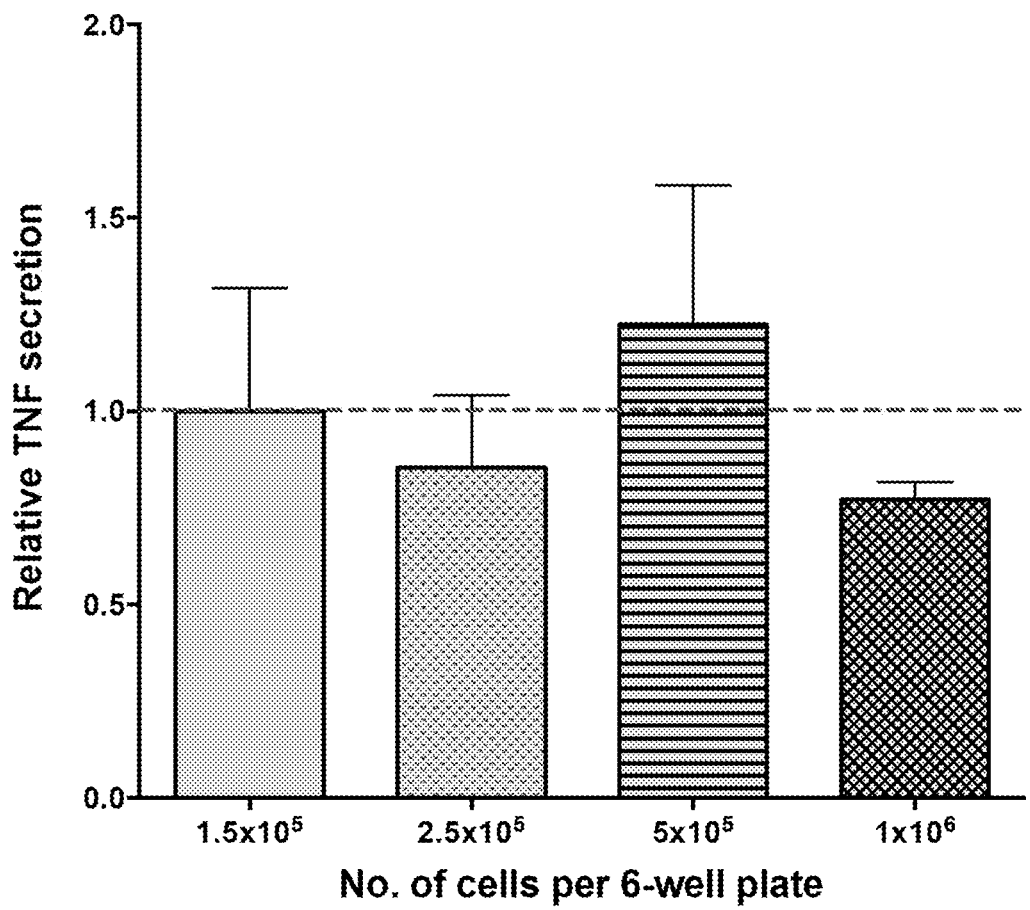

FIG. 5B: Cytokine levels do not depend on cell concentration. TNF secreted by varying numbers of freshly disaggregated cells from Dupuytren's nodules incubated for 24 hours in 4 ml of culture medium (DMEM) and 5% fetal bovine serum. The levels of TNF were determined by ELISA.

Figure 5C:
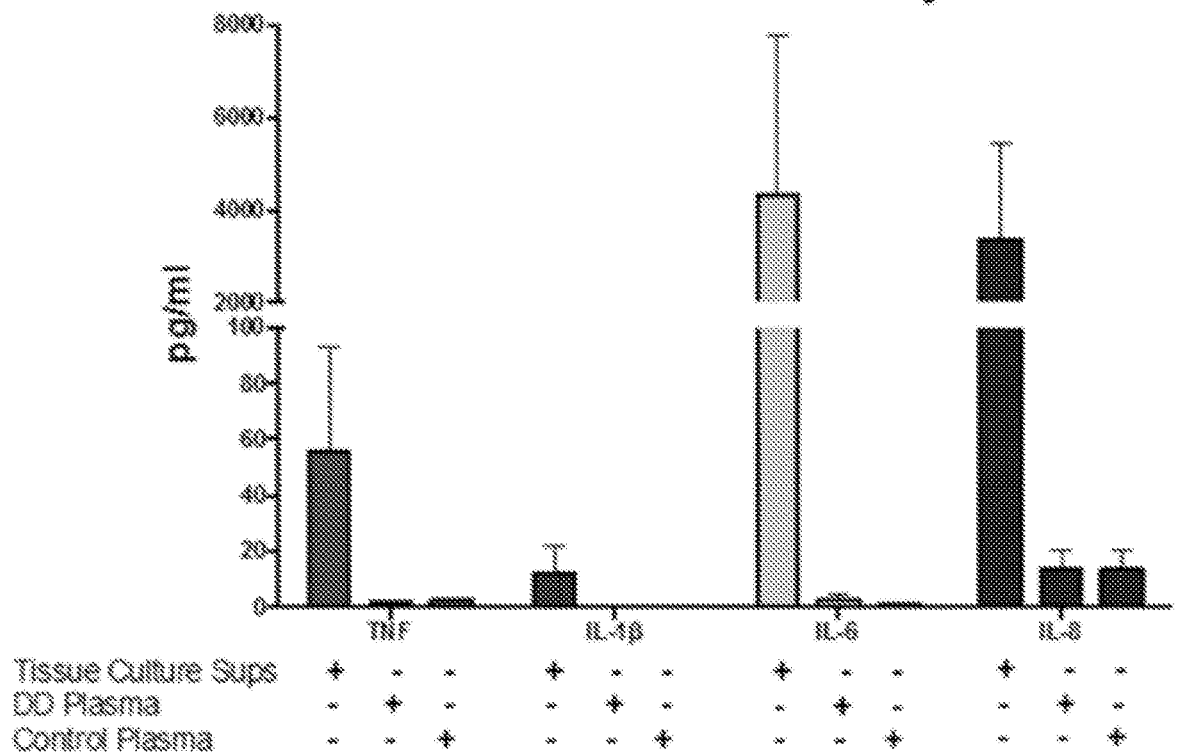

FIG. 5C: Cytokines in the plasma of patients with Dupuytren's disease compared with those secreted by freshly disaggregated nodular cells. Plasma levels of TNF, IL-1β, IL-6 and IL-8 were much lower in the systemic circulation.

Figure 5D:
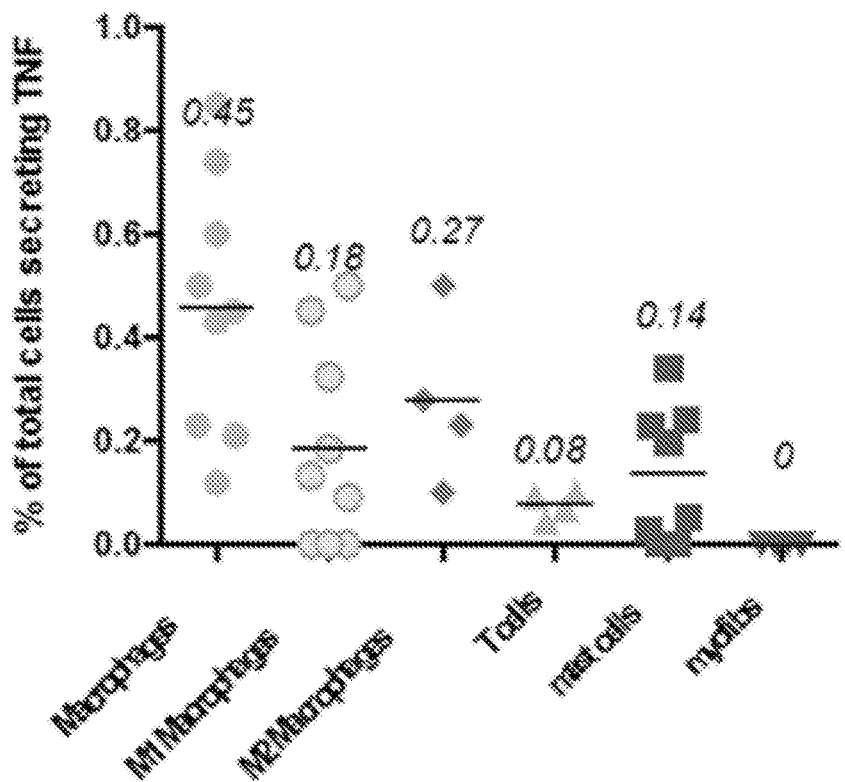

FIG. 5D: Characterization of cells in Dupuytren's nodules secreting TNF. The cells expressing TNF by FACS included macrophages, both classically and alternatively activated mast cells and T cells.

Figure 5E:
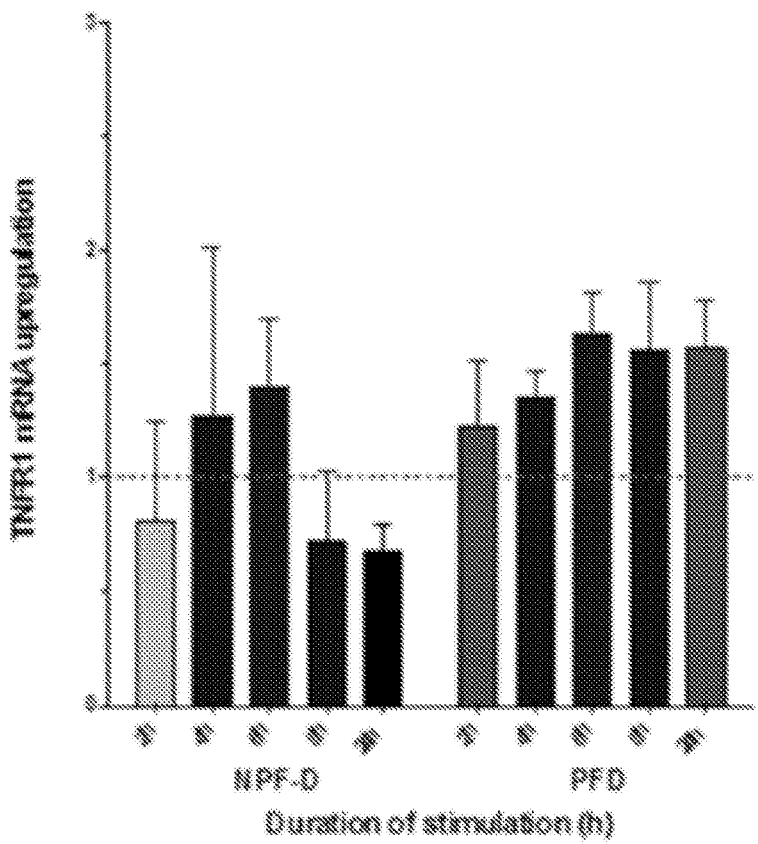
Figure 5E:
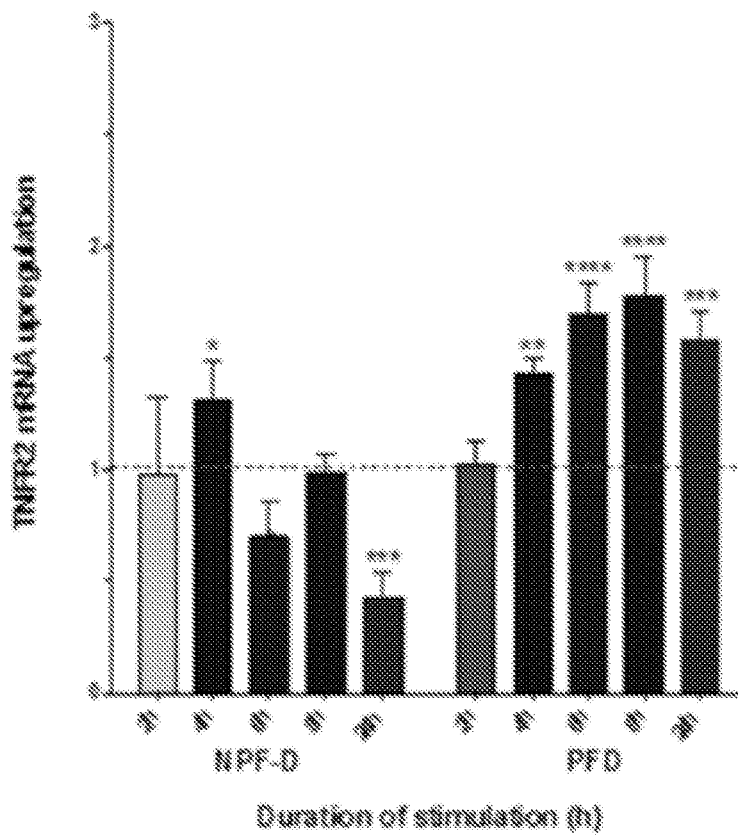
Figure 5F:

FIGS. 5E and 5F: Palmar dermal fibroblasts but not non-palmar dermal fibroblasts from the same individuals with Dupuytren's disease show increased expression of TNFR2 but not TNFR1 on treatment with TNF. Dupuytren's disease only occurs in the palm of genetically susceptible individuals. Exposure to physiologically relevant levels (0.1 ng/ml) of TNF of the palmar dermal fibroblasts from these patients resulted in increased expression of the inducible TNFR2 whilst expression of TNFR1 is reduced in these cells at both mRNA and protein level when exposed.

Figure 5G:
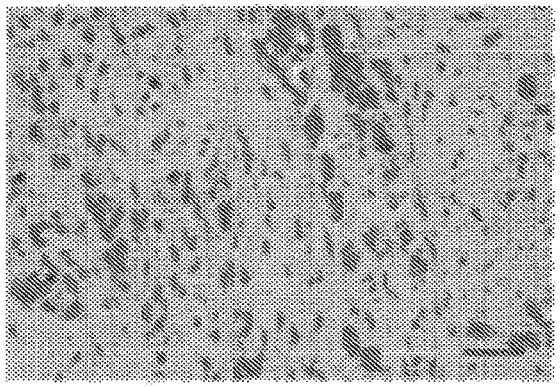
Figure 5G:
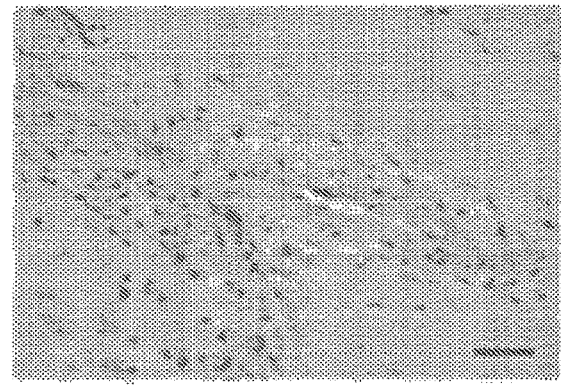
Figure 5G:
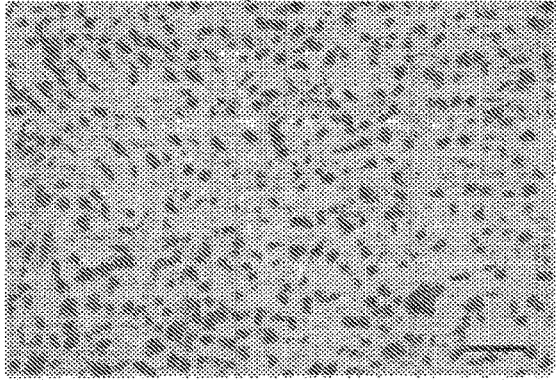
Figure 5G:
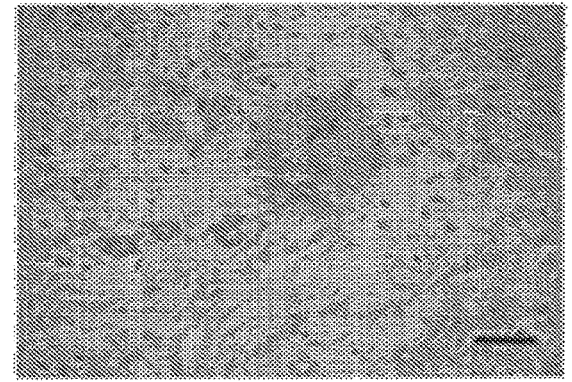

FIG. 5G: Immunostaining of TNFR1 and TNFR2 in Dupuytren's nodules. The majority of the cells in Dupuytren's nodules express both TNFR1 and TNFR2.

Figure 5H:
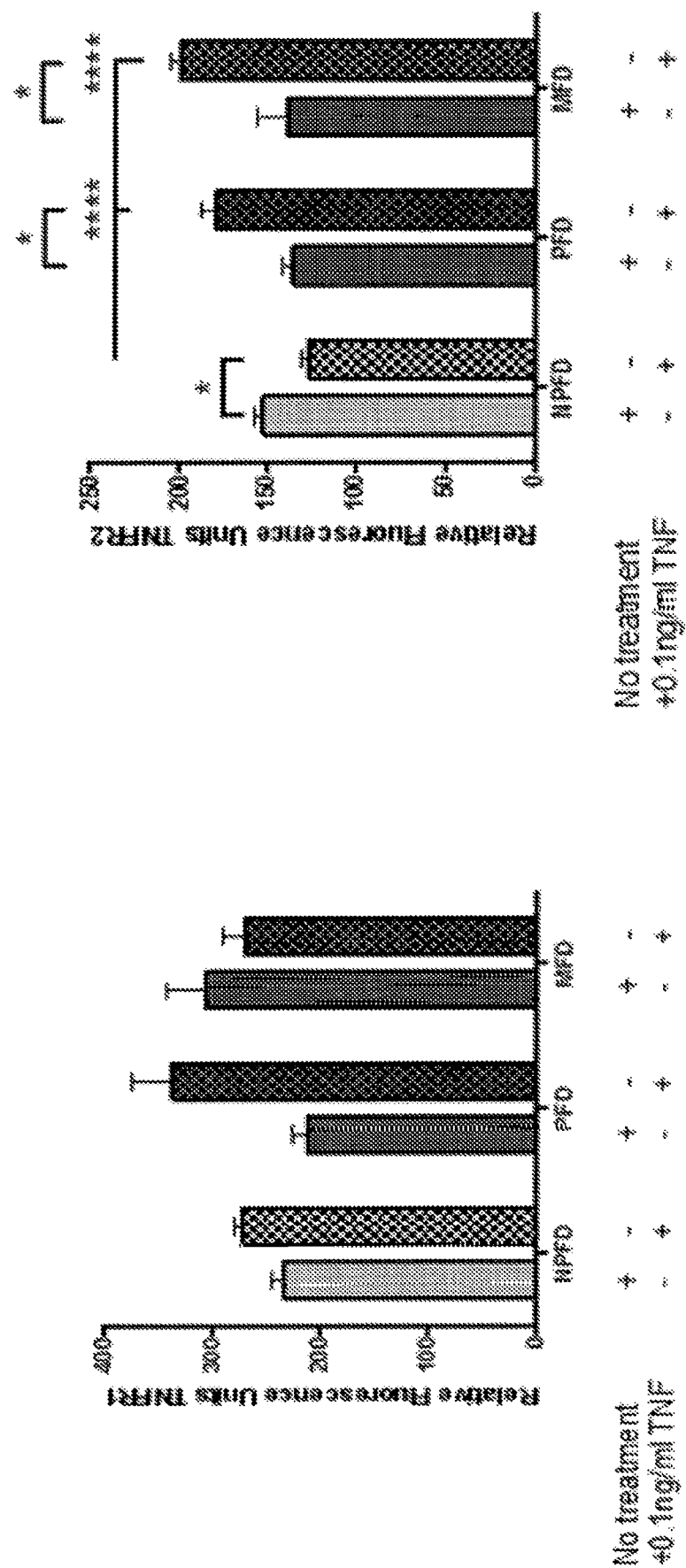

FIG. 5H: Palmar dermal fibroblasts and myofibroblasts show increased expression of TNFR2 but not TNFR1 on treatment with TNF. Non-palmar dermal fibroblasts from the same individuals with Dupuytren's disease show decreased expression of TNFR2. Quantification of immunofluorescent staining of matched cells from 3 donors. 20 cells were assessed from each patient.

FIGS. 6A-6F: IL-33 produced by myofibroblasts acts on mast cells and alternatively activated (M2) macrophages leading to increased TNF expression.

Figure 6A:
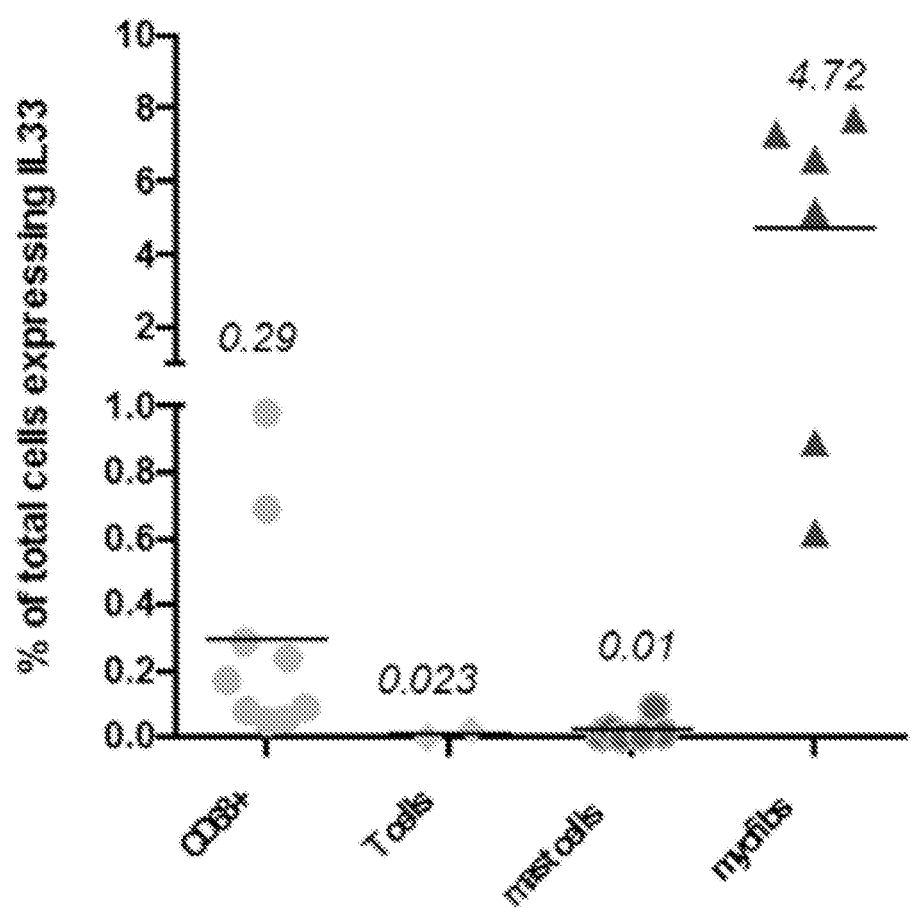

FIG. 6A: Myofibroblasts from Dupuytren's nodules express IL-33. The majority of the cells expressing IL-33 by FACS are myofibroblasts.

Figure 6B:
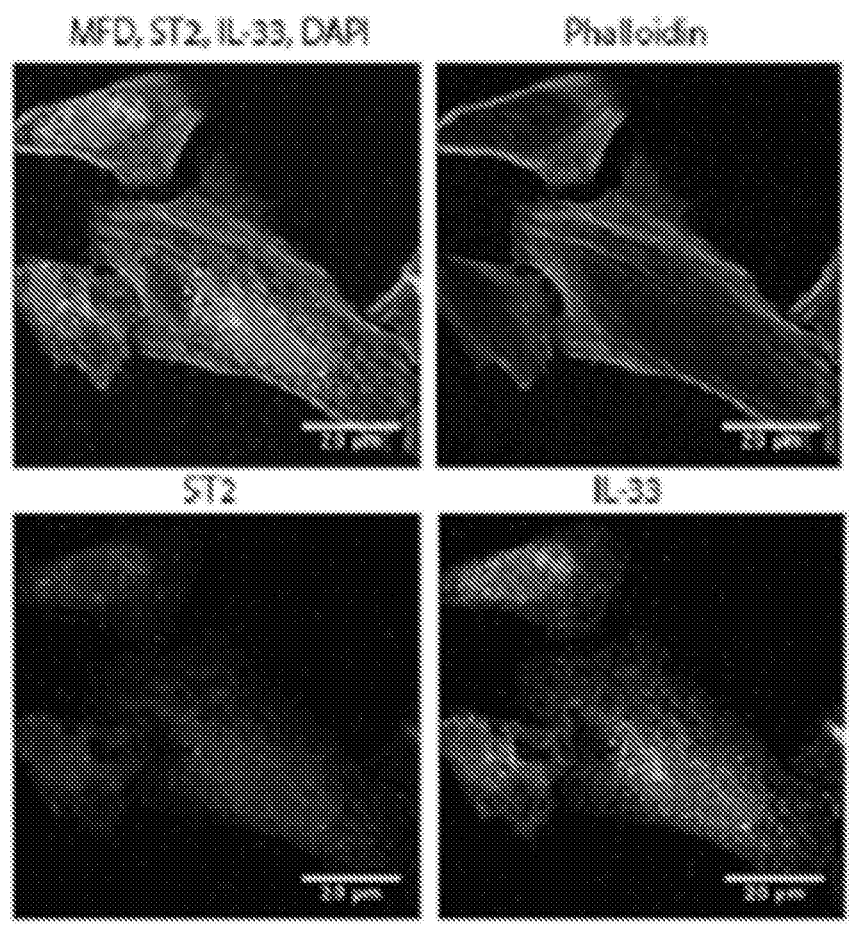

FIG. 6B: Immunofluorescence staining of ST2 and IL-33 freshly isolated myofibroblasts from Dupuytren's nodules. ST2 labels the cell surface whilst the IL-33 is seen both within the nucleus and cytoplasm.

Figure 6C:
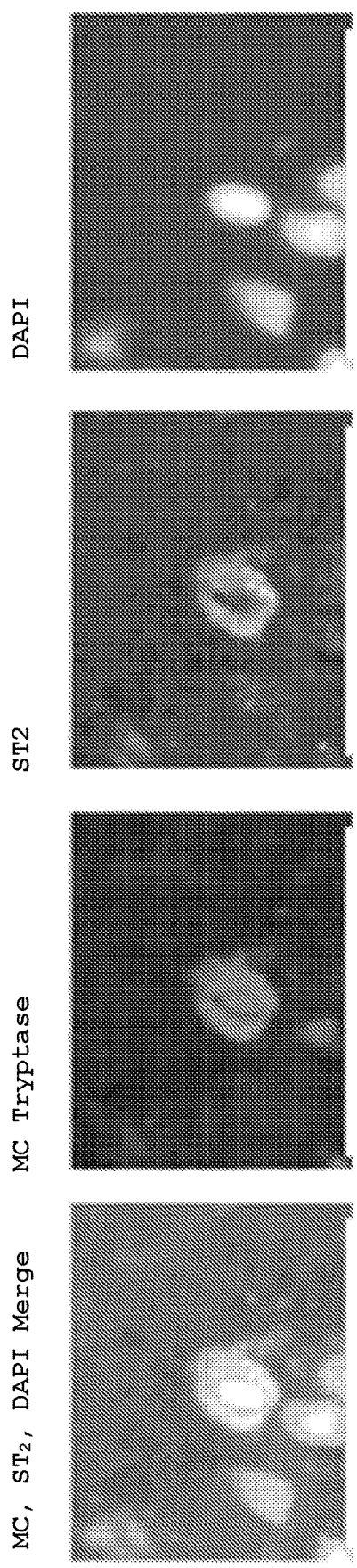
Figure 6C:
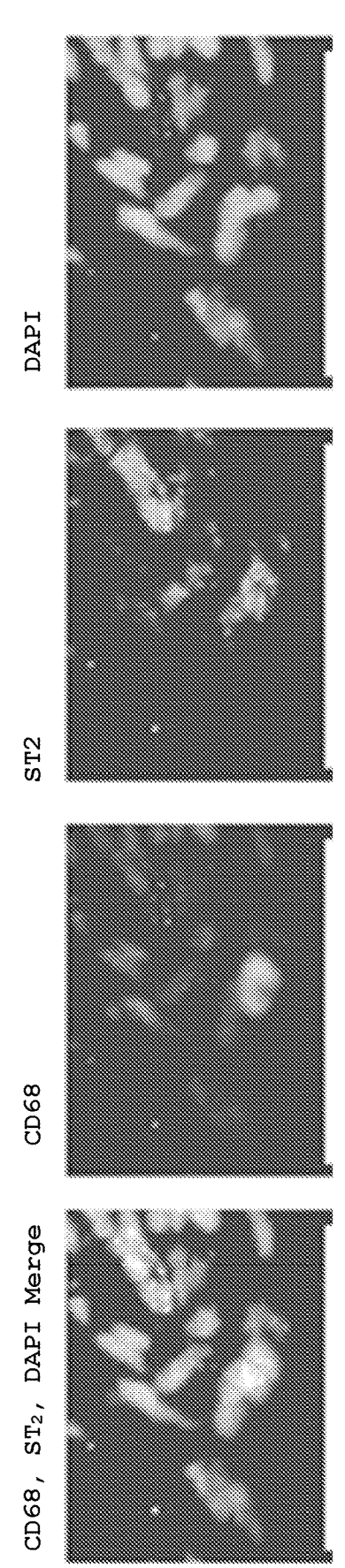

FIG. 6C: Freshly isolated mast cells and macrophages from Dupuytren's nodules express ST2, the receptor for IL-33. Immunofluorescence co-staining.

Figure 6D:
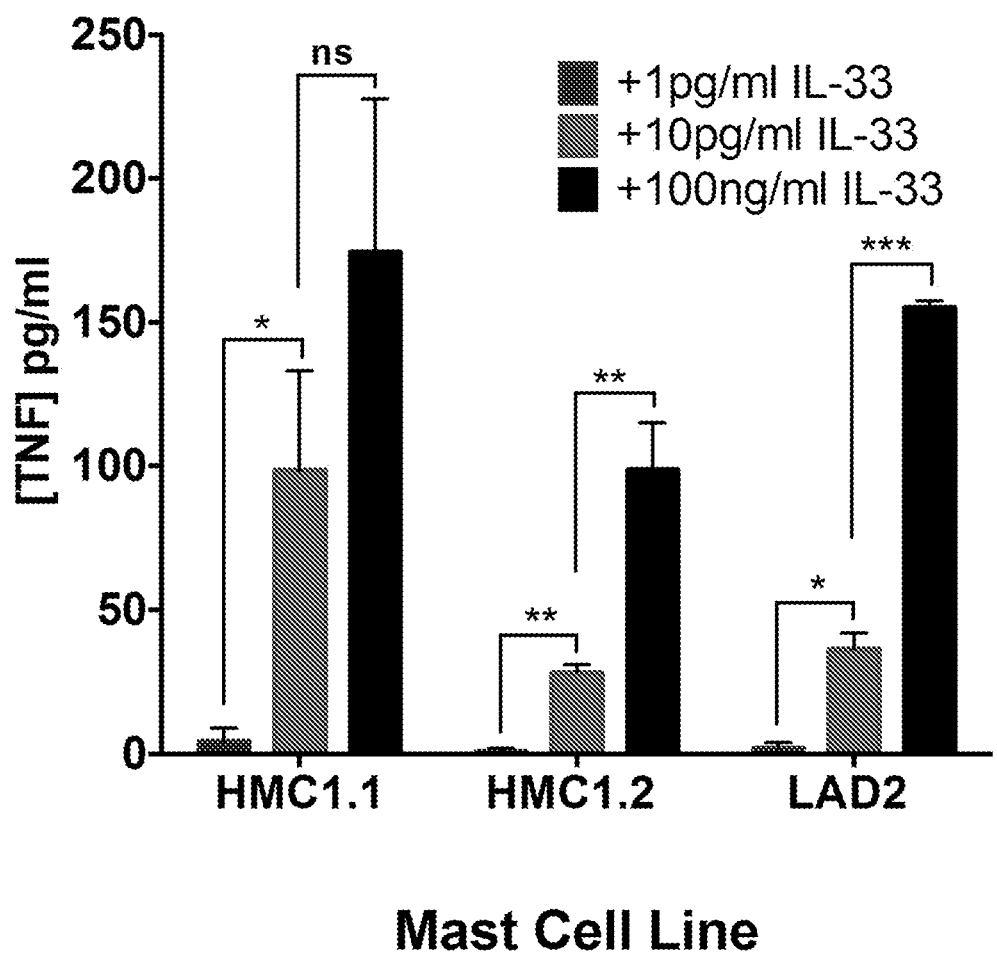

FIG. 6D: Mast cell lines show increased TNF secretion on exposure to IL-33 in a dose-dependent manner.

Figure 6E:
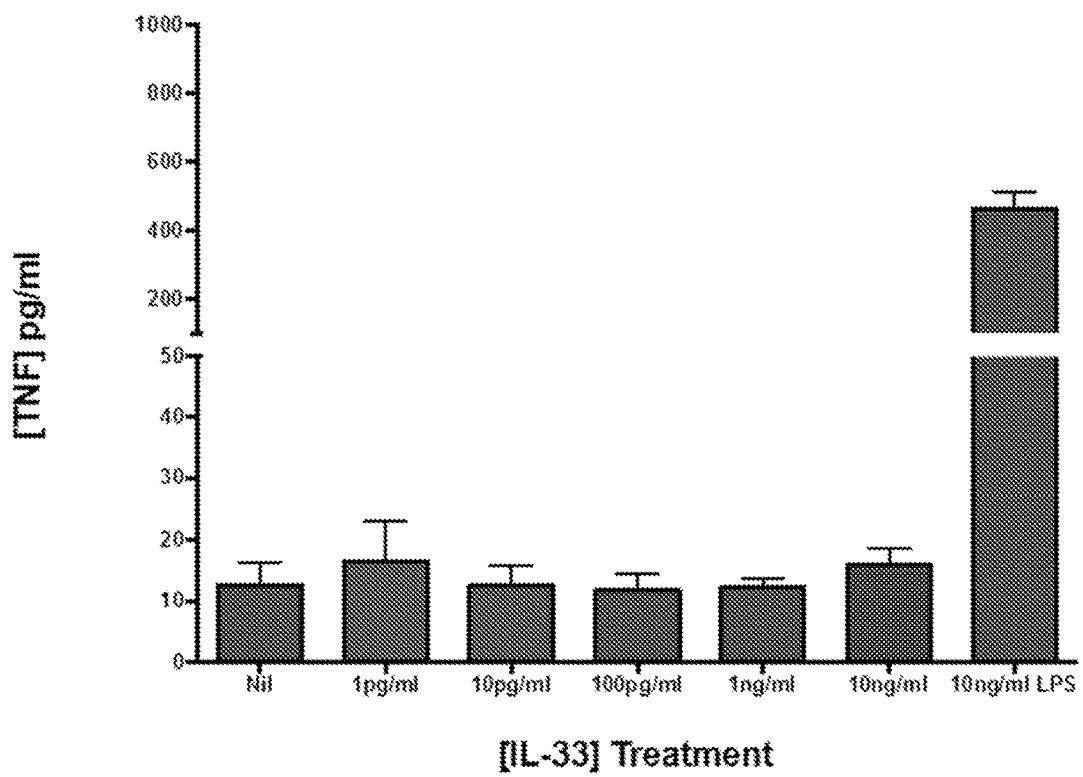
Figure 6E:
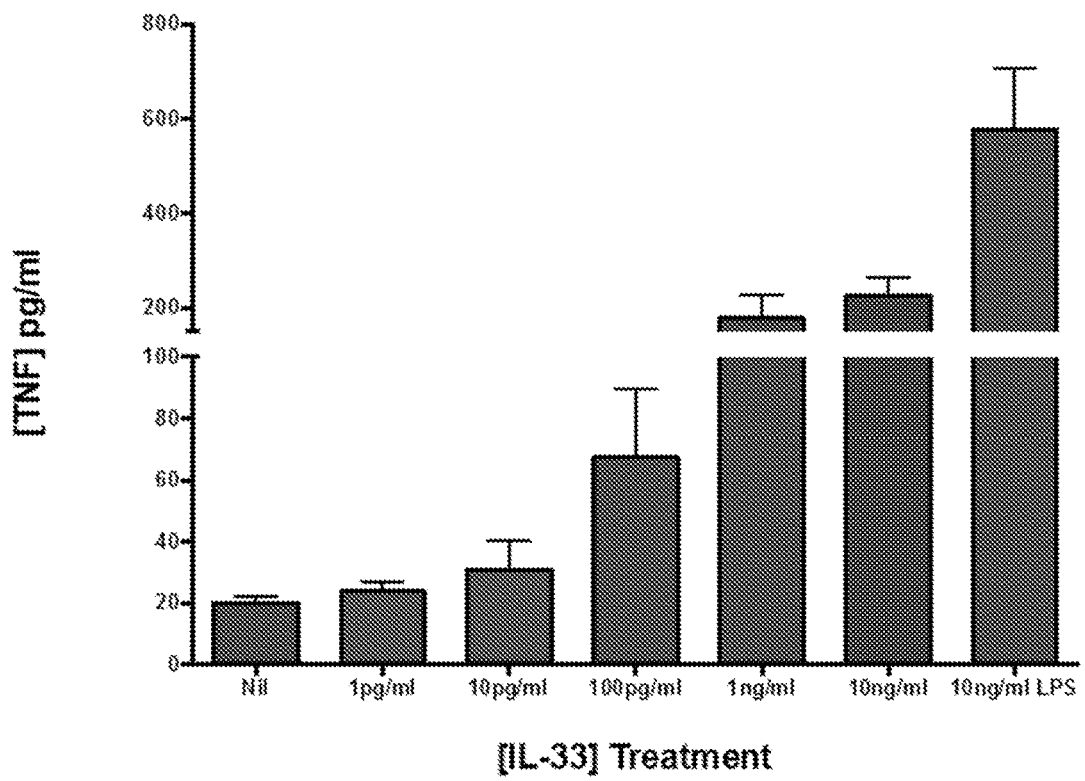
Figure 6F:
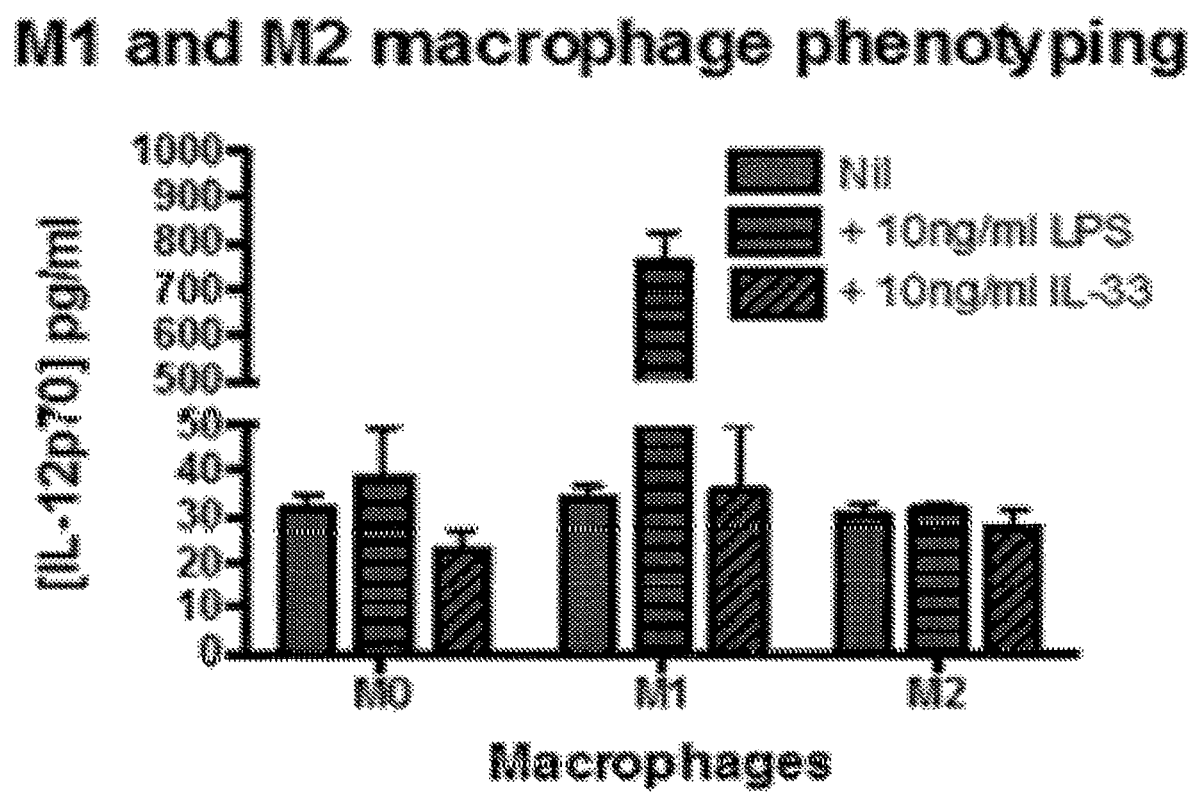

FIGS. 6E and 6F: Only alternatively activated macrophages (M2) derived from human monocytes and pre-treated with TNF show increased secretion of TNF on exposure to IL-33 in a dose-dependent manner.

FIGS. 7A-7F: Palmar fibroblasts but not non-palmar fibroblasts from patients with Dupuytren's disease differentiate into myofibroblasts and show increased expression of IL-33 and ST2 on exposure to TNF.

Figure 7A:
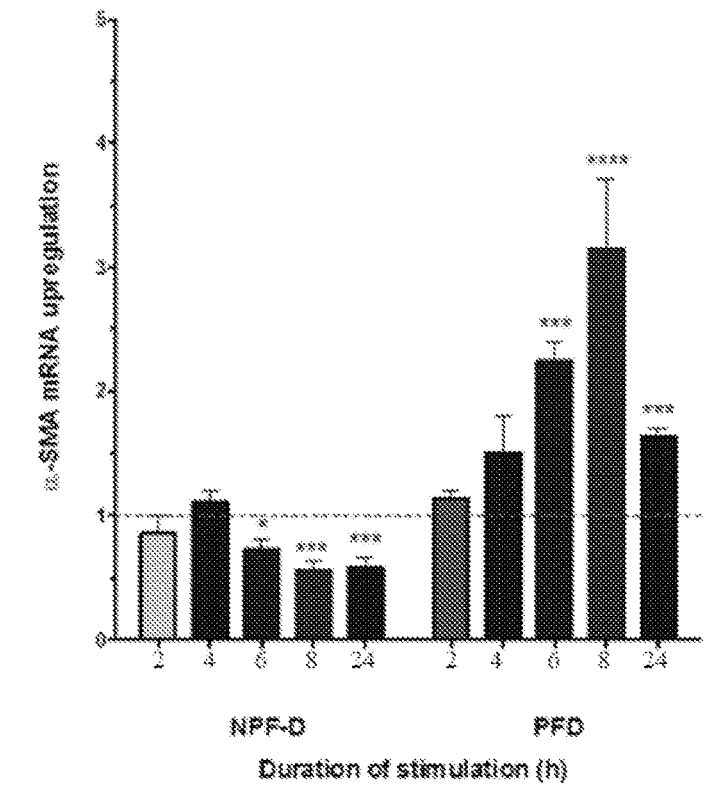
Figure 7A:
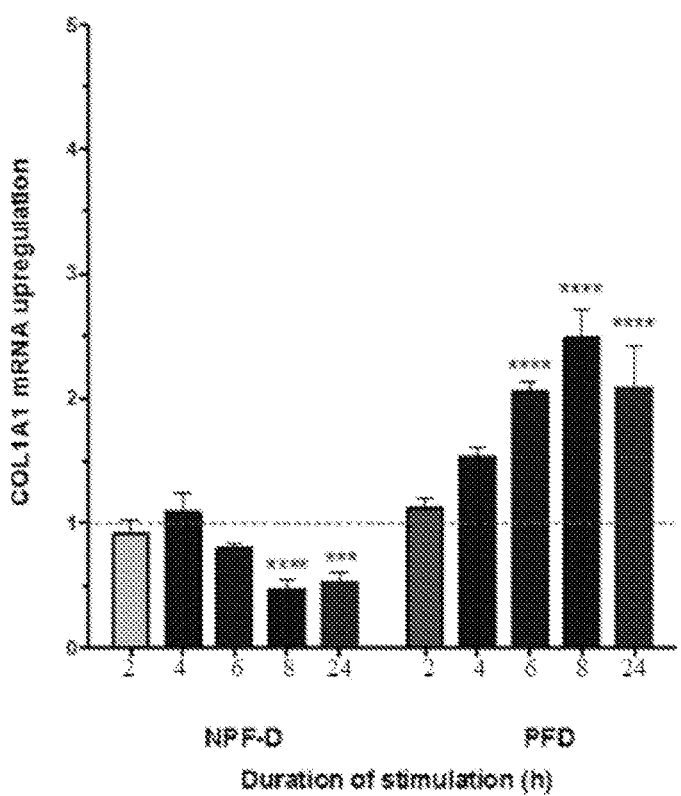
Figure 7B:
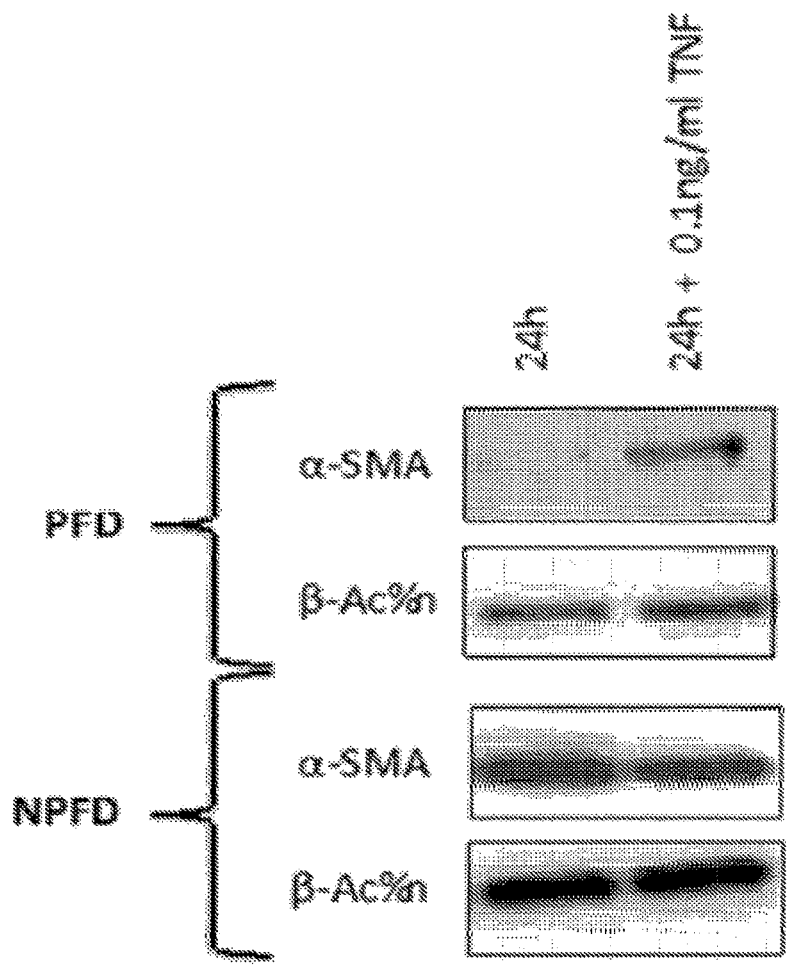

FIGS. 7A and 7B: Only palmar fibroblast differentiate into myofibroblasts as evidenced by increased α-SMA at mRNA and protein levels and increased COL1A1 mRNA expression on treatment with 0.1 ng/ml TNF.

Figure 7C:
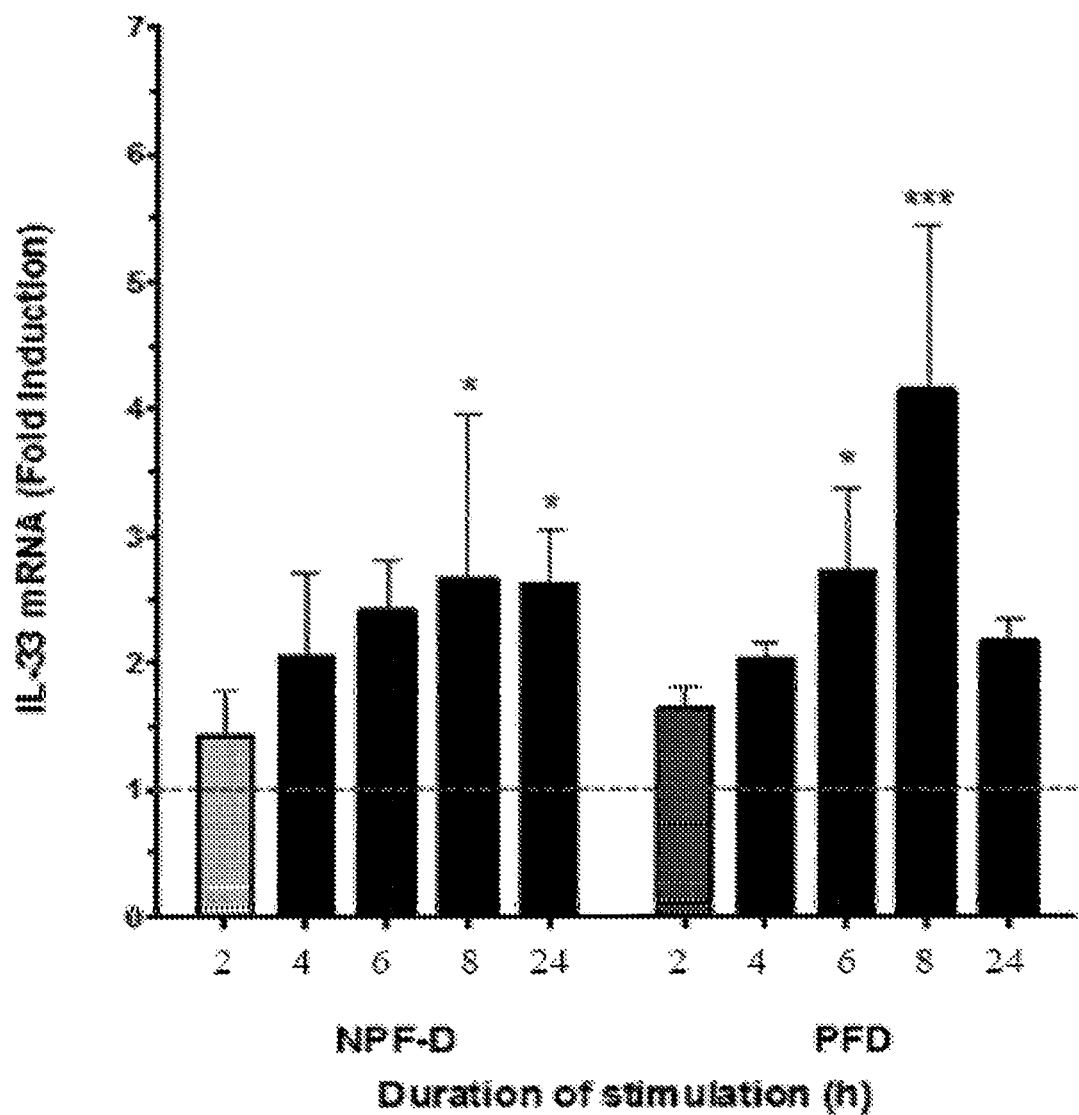
Figure 7D:
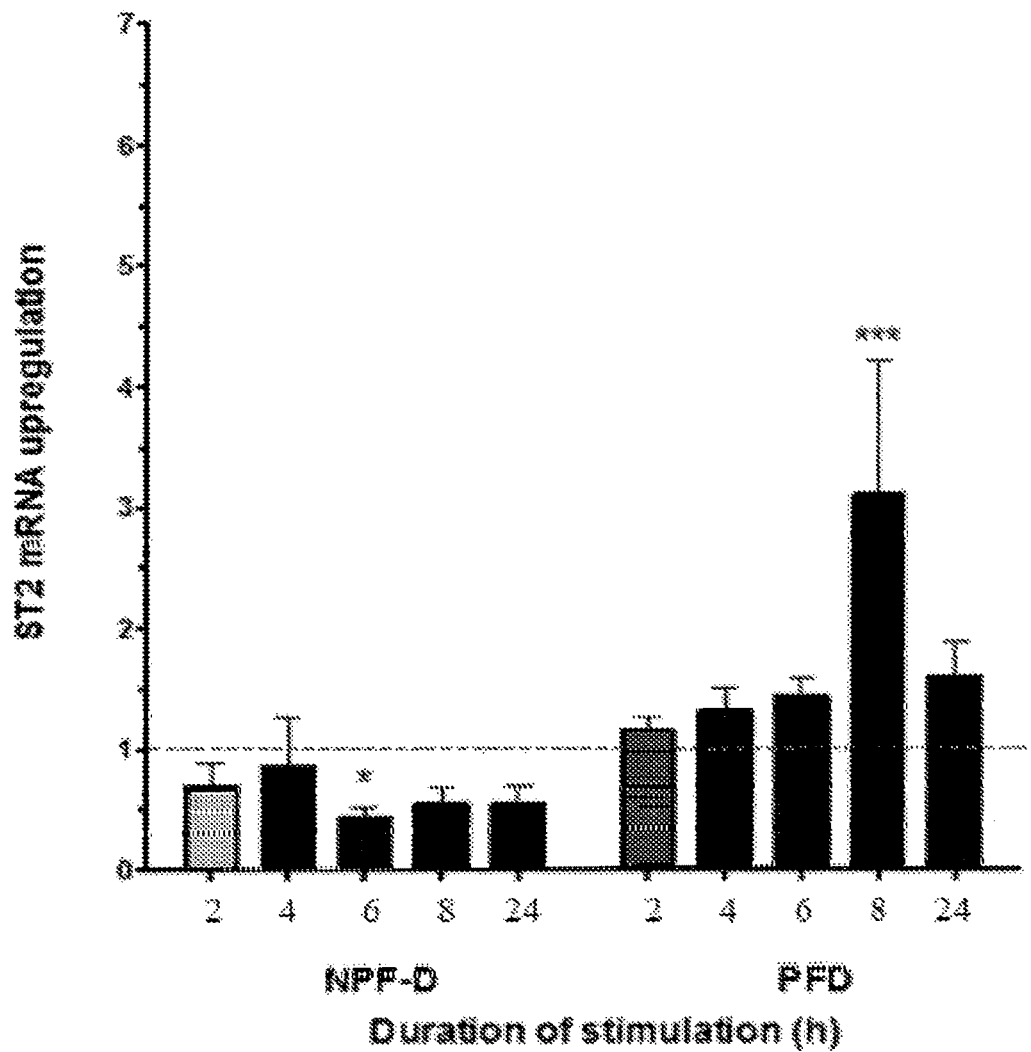
Figure 7E:
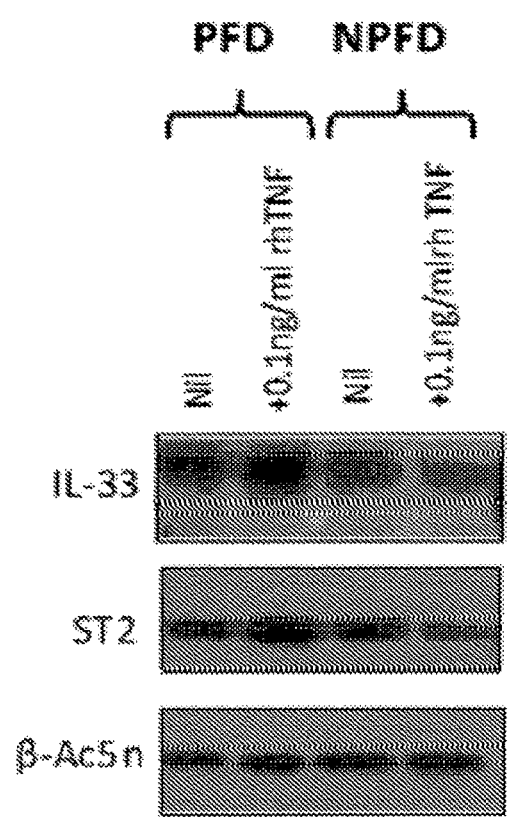

FIGS. 7C-7E: Only palmar fibroblast show increased expression of IL-33 and ST2 at both mRNA and protein levels whilst non-palmar fibroblasts show reduced expression of ST2 on exposure to TNF.

Figure 7F:
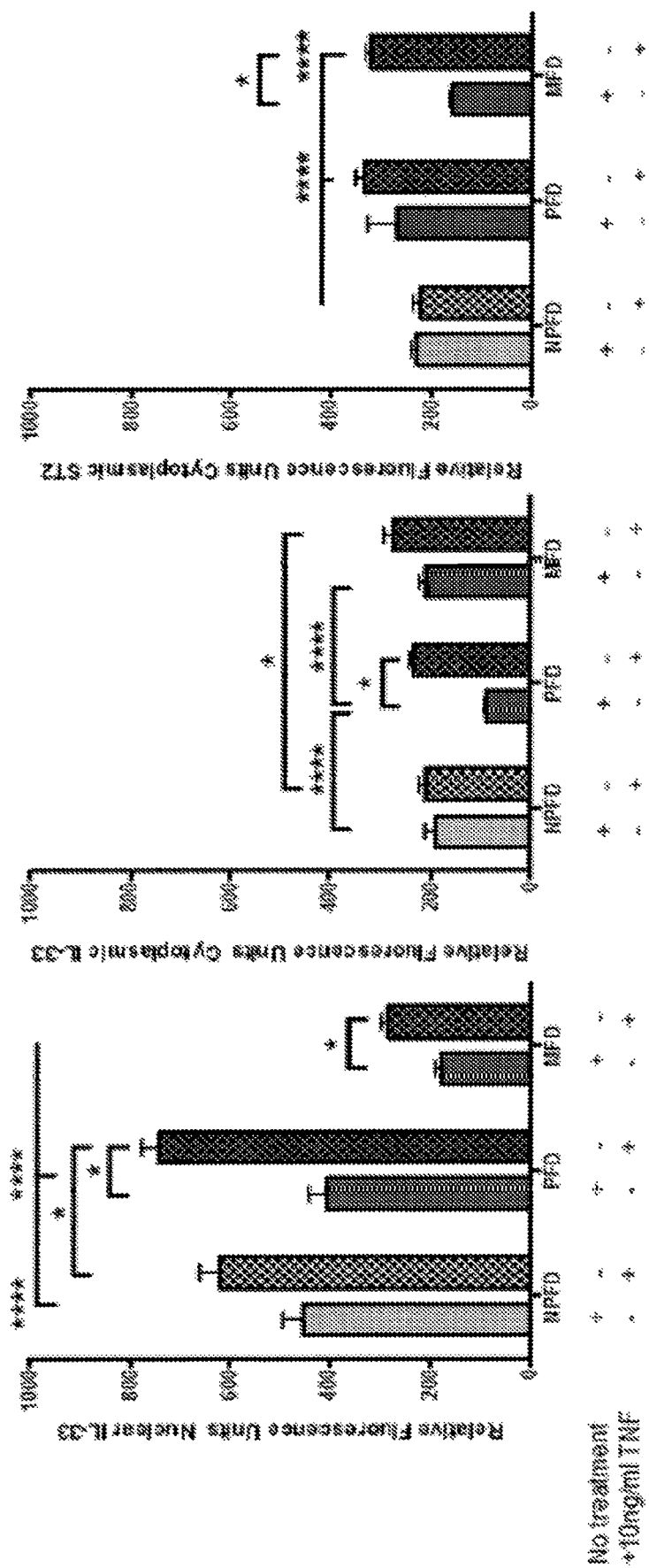

FIG. 7F: Palmar fibroblasts show increased expression of nuclear and cytoplasmic IL-33 and ST2 on treatment with TNF. Quantification of immunofluorescent staining of matched cells from 3 donors. 20 cells of each type were assessed from every patient.

FIGS. 8A-8I: Inhibition of TNF, TNFR2 or IL-33 down regulates the myofibroblast phenotype, with a combination of TNFR2 and IL-33 being most effective.

Figure 8A:
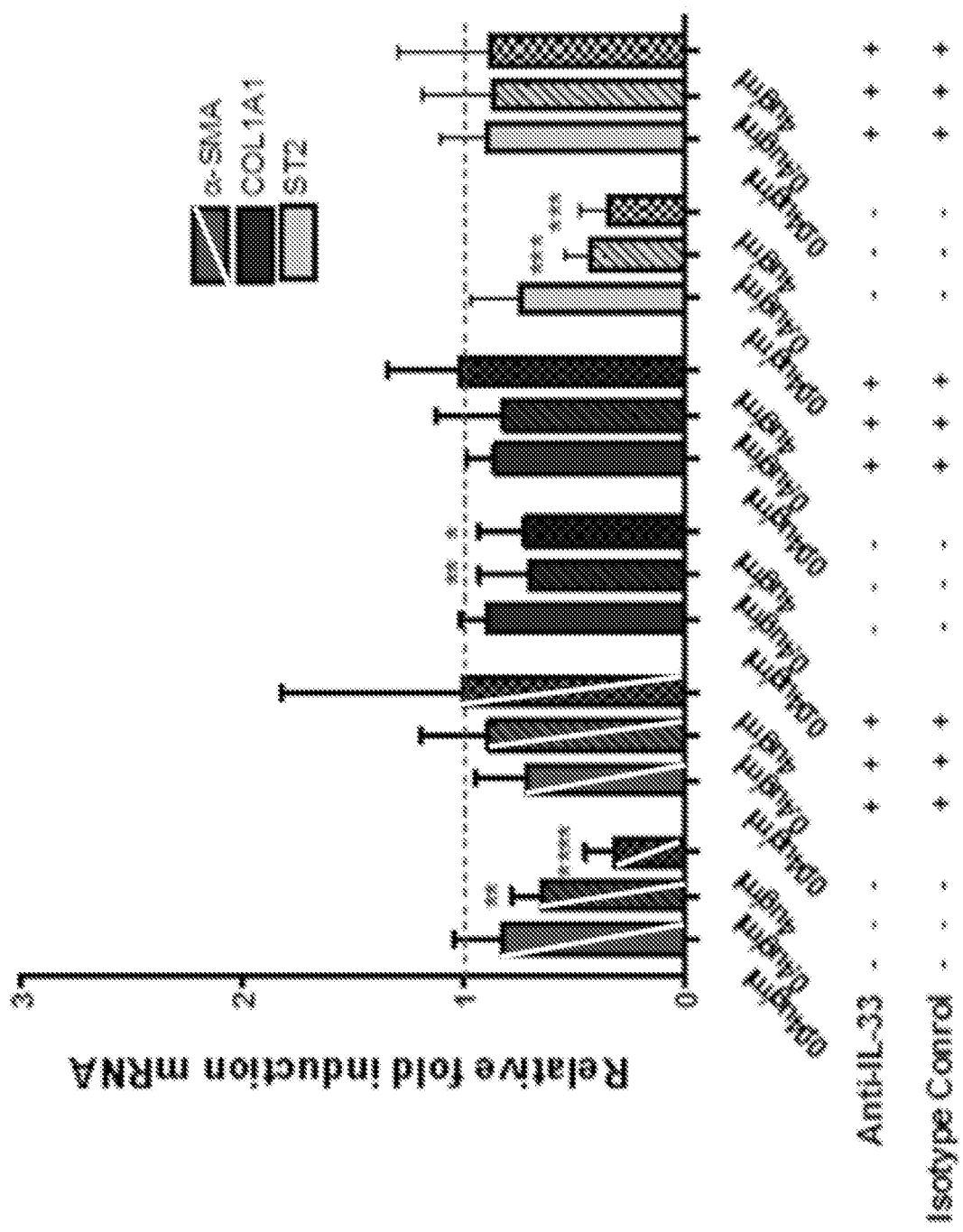
Figure 8B:
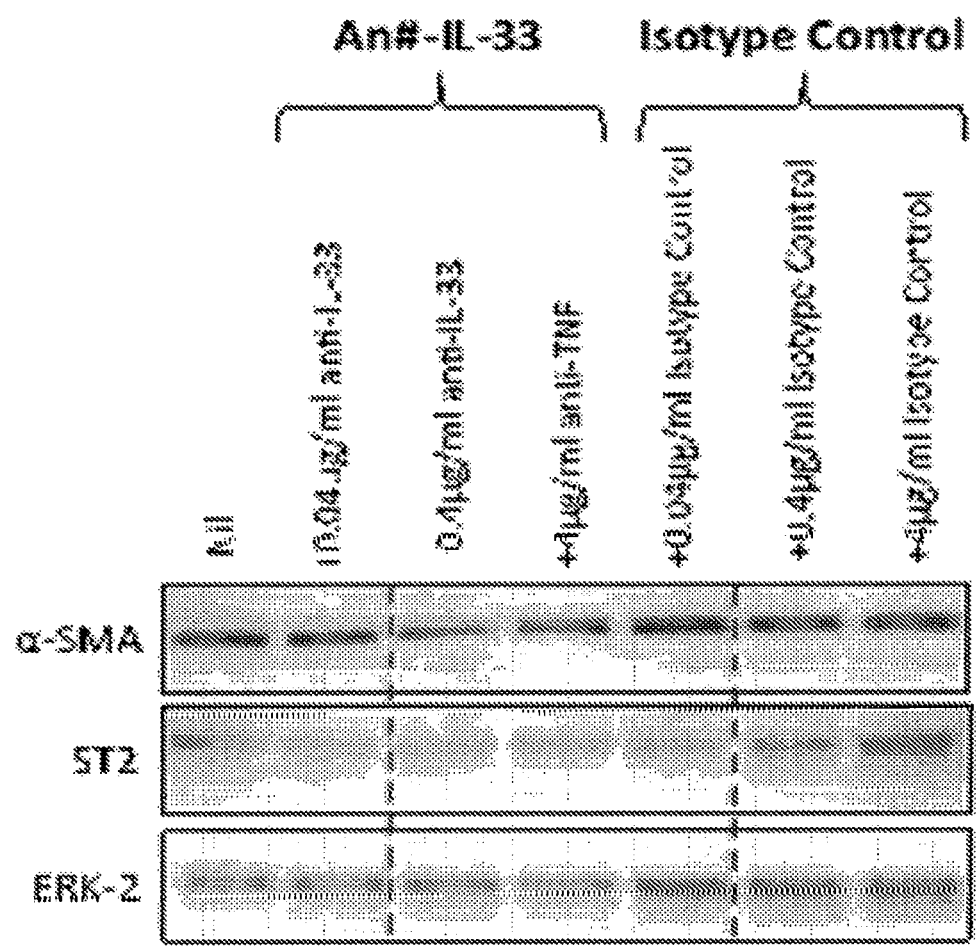

FIGS. 8A and 8B: Anti-IL-33 down regulates the expression of α-SMA and ST2 at both the mRNA and protein level and COL1A1 at the mRNA level in myofibroblasts from patients with Dupuytren's disease in a dose-dependent manner. Data from non-responders not shown.

Figure 8C:
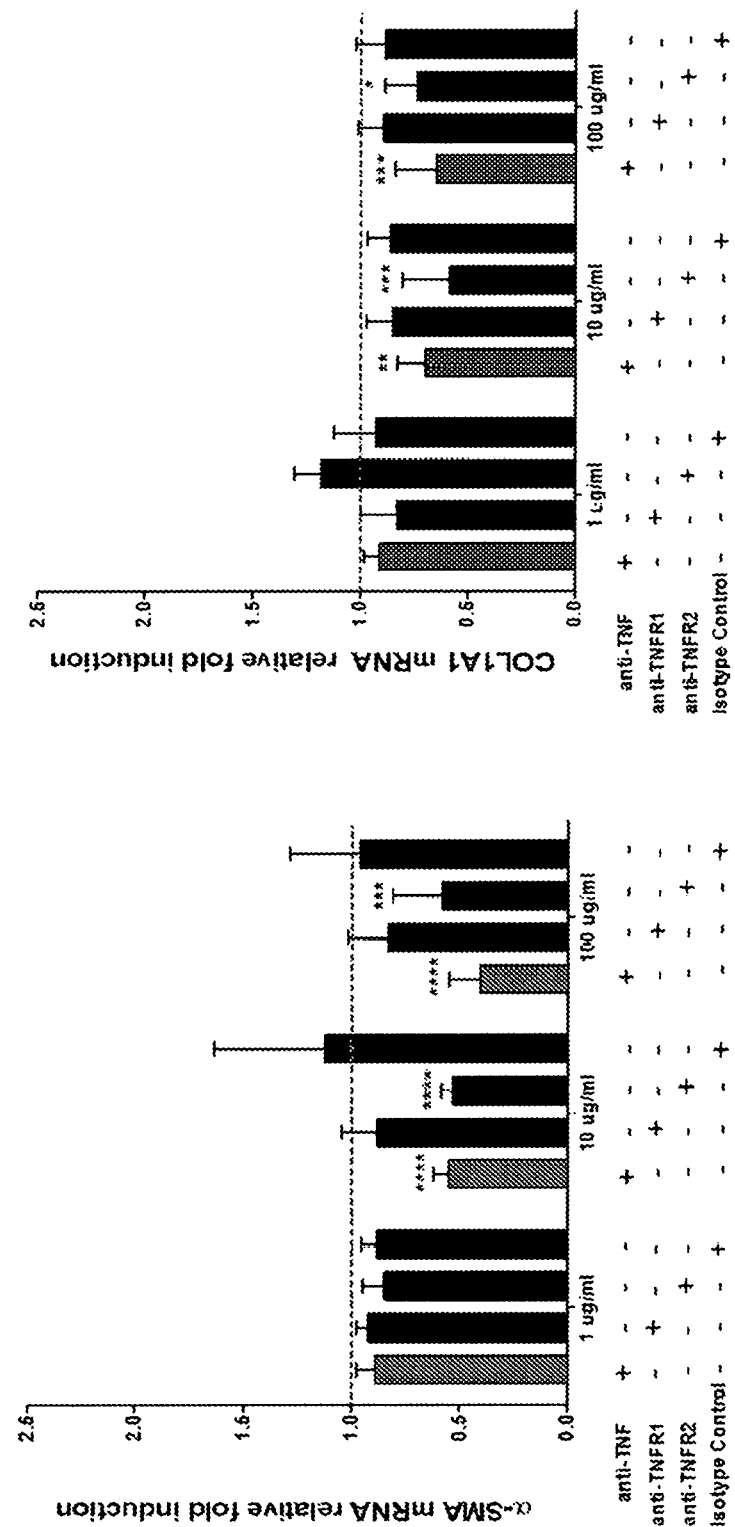
Figure 8D:
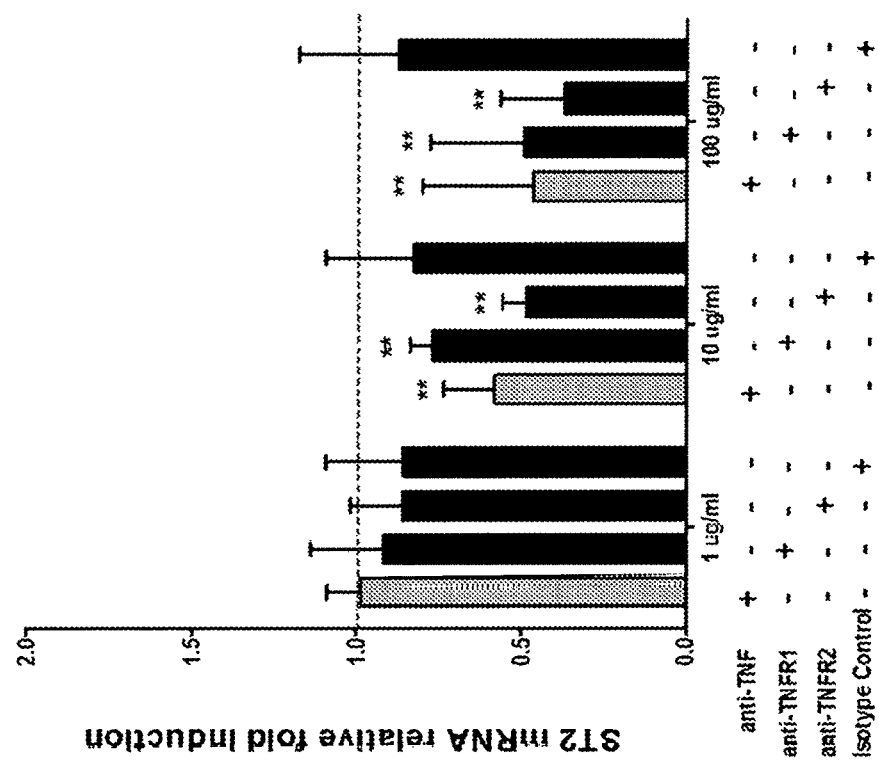
Figure 8D:
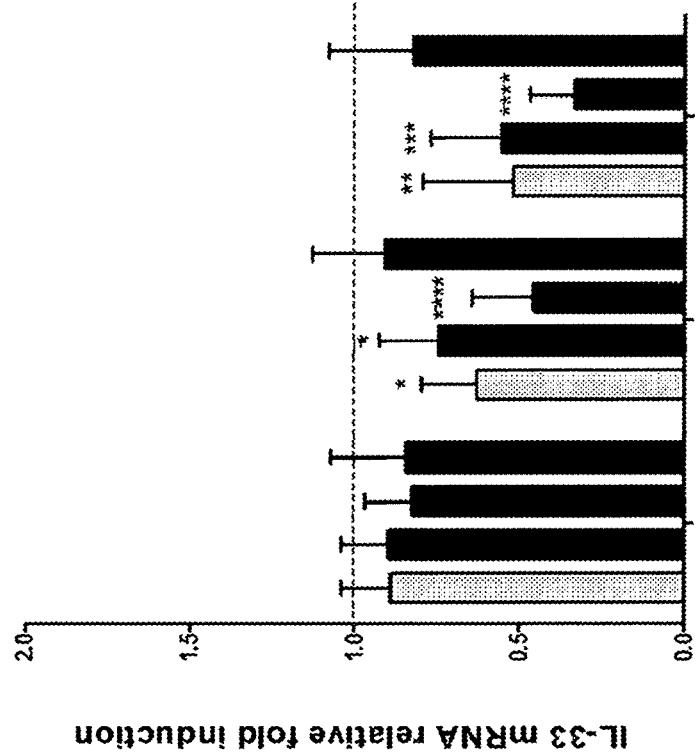
Figure 8E:
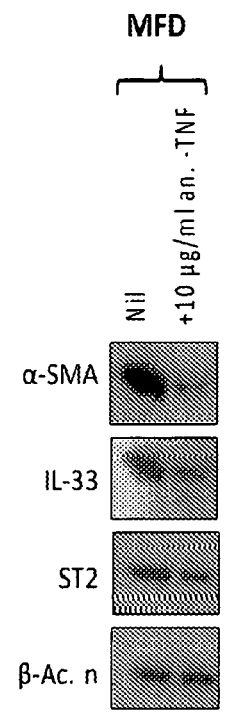

FIGS. 8C-8E: Only inhibition of TNF or TNFR2 but not TNFR1 down-regulates the expression of α-SMA, COL1-A1, IL-33 and ST2 at mRNA level and 11-33 and ST2 also at protein level in myofibroblasts from responsive myofibroblasts from patients with Dupuytren's disease. Data from non-responders not shown.

Figure 8F:
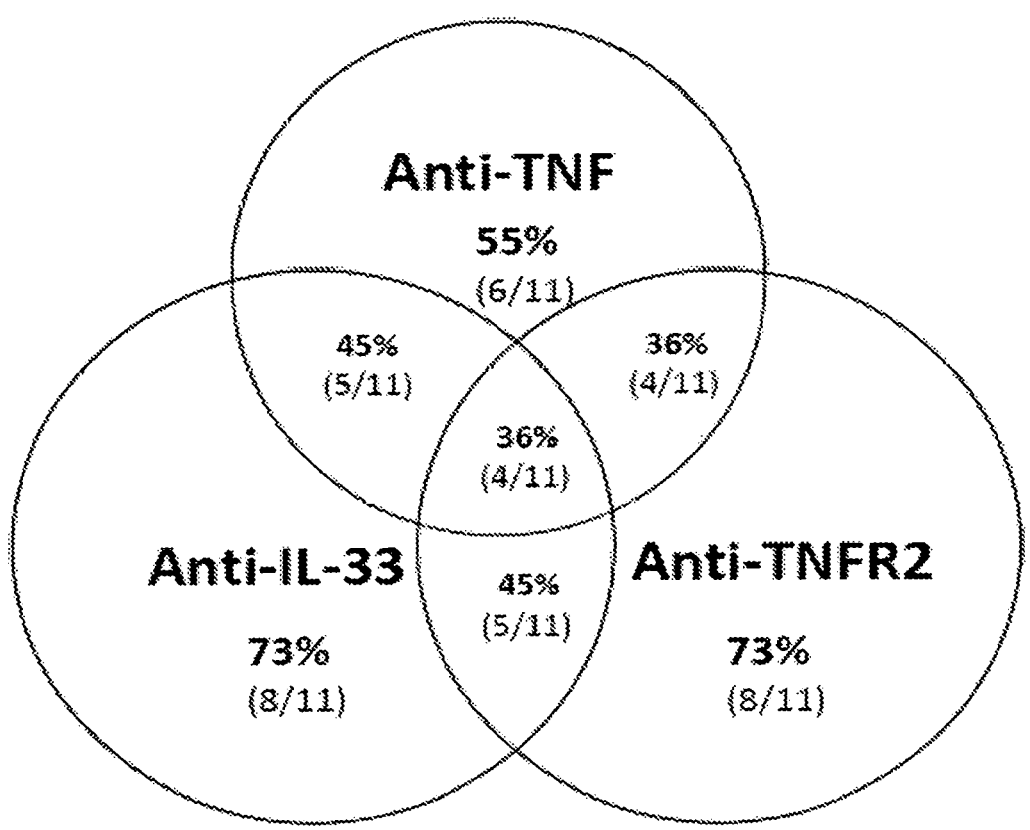

FIG. 8F: Venn diagram showing the relative efficacy of TNF or IL-33 or TNFR2 inhibition. α-SMA was down regulated in myofibroblasts 6 of 11 patient samples (55%) by anti-TNF, 8 of 11 patient samples (73%) by anti-IL-33 and in 8 of 11 samples by anti-TNFR2. Therefore, combined anti-TNF and anti-IL-33 would be effective in 9 out of 11 patient samples (82%) and anti-TNFR2 and anti-IL-33 in 11 of 11 samples (100%).

Figure 8G:
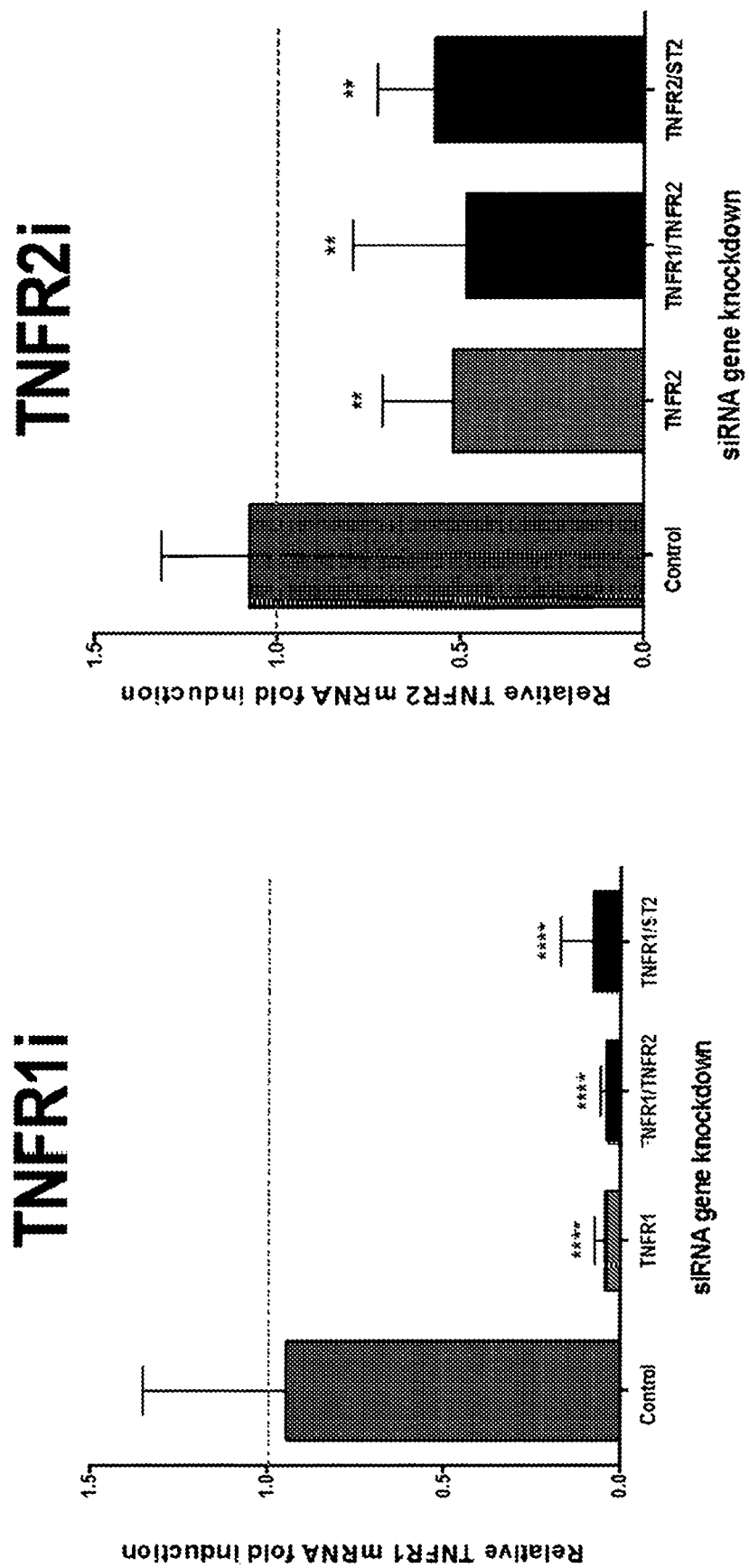
Figure 8H:
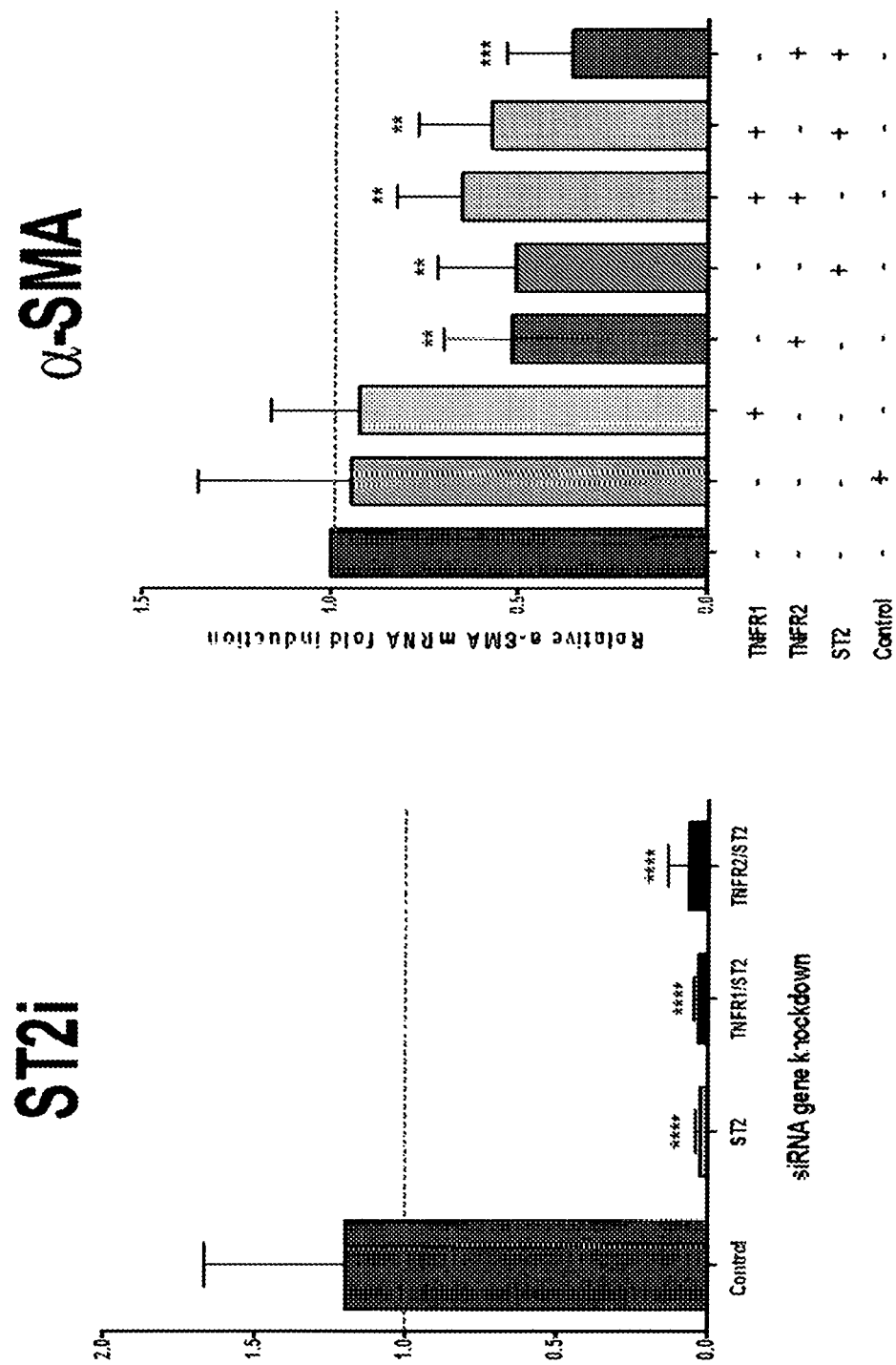
Figure 8I:
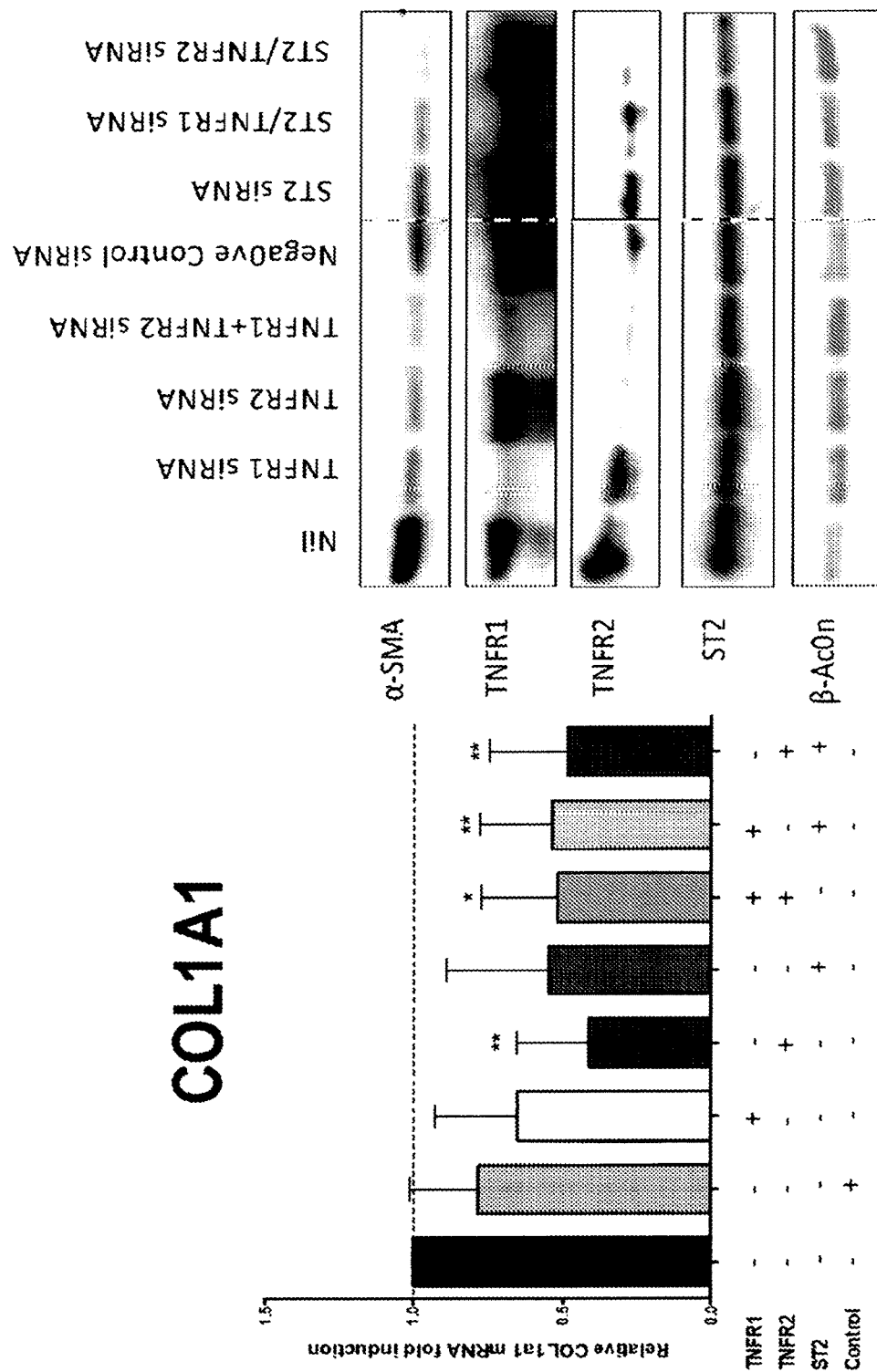

FIGS. 8G-8I: Inhibition of expression of TNFR2, ST2 and most effectively TNFR2+ST2 down regulates myofibroblast phenotype.

Figure 9:
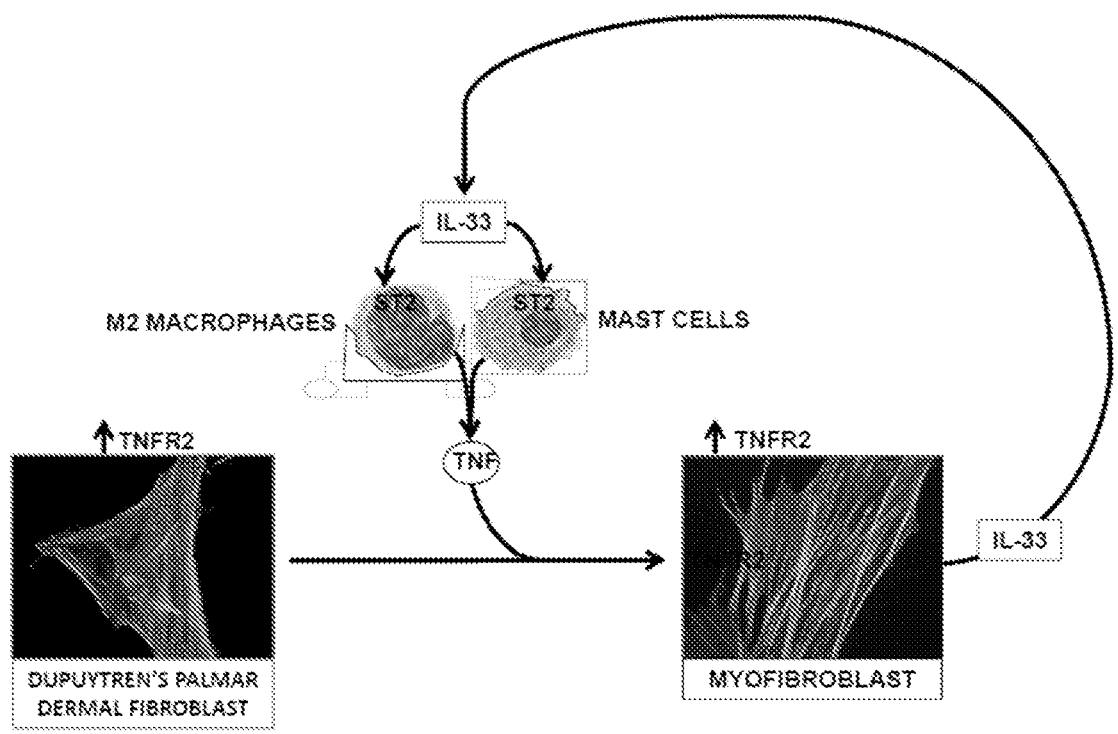

FIG. 9: Proposed mechanism of action of IL-33. TNF secreted by resident immune cells, including macrophages and mast cells, converts precursor cells into myofibroblasts. As the cells differentiate into myofibroblasts, they secrete IL-33. This in turn acts on the immune cells, leading to further TNF production through a positive feedback loop, resulting in chronic localized inflammation and a fibrotic response.

Figure 10:
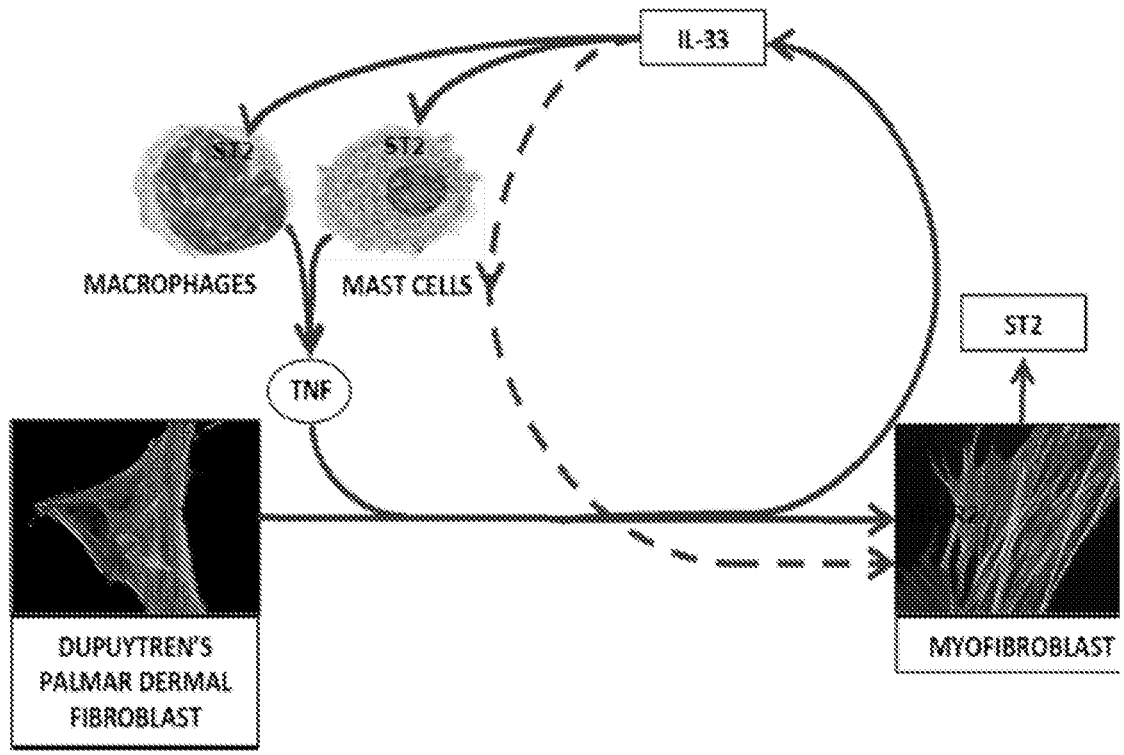

FIG. 10: Proposed mechanism of action of IL-33. TNF secreted by resident immune cells, including macrophages and mast cells, converts precursor cells into myofibroblasts. As the cells become myofibroblasts, they secrete IL-33, which acts on the immune cells, leading to further TNF production, driving a positive feedback loop and a chronic fibrotic response. The IL-33 also acts on the myofibroblasts via ST2 and further enhances IL-33 expression.

DETAILED DESCRIPTION OF THE INVENTION

The subject invention provides a method of treating a patient suffering from a localized fibrotic condition which comprises administering to the patient an amount of an IL-33 antagonist effective to treat the patient.

The subject invention also provides a method of treating a patient suffering from a localized fibrotic condition which comprises administering to the patient an amount of an ST2 antagonist effective to treat the patient.

In one embodiment, the localized fibrotic condition is selected from the group consisting of Dupuytren's disease, frozen shoulder (adhesive capsulitis), periarticular fibrosis, keloid or hypertrophic scars, endometriosis, abdominal adhesions, perineural fibrosis, Ledderhose disease, Peyronie's disease, peritendinous adhesions, and periarticular fibrosis. In another embodiment, the localized fibrotic condition is selected from the group consisting of Dupuytren's disease, frozen shoulder (adhesive capsulitis), periarticular fibrosis, keloid or hypertrophic scars, endometriosis, abdominal adhesions, and perineural fibrosis.

In one embodiment, the localized fibrotic condition is Dupuytren's disease. In another embodiment, the localized fibrotic condition is early disease stage Dupuytren's disease. In another embodiment, the localized fibrotic condition is established disease stage Dupuytren's disease. In another embodiment, the localized fibrotic condition is frozen shoulder (adhesive capsulitis). In another embodiment, the localized fibrotic condition is periarticular fibrosis. In another embodiment, the localized fibrotic condition is keloid or hypertrophic scars. In another embodiment, the localized fibrotic condition is endometriosis. In another embodiment, the localized fibrotic condition is abdominal adhesions. In another embodiment, the localized fibrotic condition is perineural fibrosis. In another embodiment, the localized fibrotic condition is Ledderhose disease. In another embodiment, the localized fibrotic condition is Peyronie's disease. In another embodiment, the localized fibrotic condition is peritendinous adhesions. In another embodiment, the localized fibrotic condition is periarticular fibrosis. In another embodiment, the localized fibrotic condition is in the early disease stage or early disease state.

The subject invention also provides a method of treating a patient suffering from liver fibrosis which comprises administering to the patient an amount of an IL-33 antagonist effective to treat the patient.

In one embodiment, the IL-33 antagonist is
 a) an antibody, or antigen binding fragment of an antibody, that specifically binds to, and inhibits activation of, an IL-33 receptor;
 b) a soluble form of an IL-33 receptor that specifically binds to IL-33 and inhibits IL-33 from binding to the IL-33 receptor;
 c) an antisense nucleic acid that specifically inhibits synthesis of IL-33;
 d) a small molecule that specifically inhibits the activity of IL-33;
 e) a bispecific antibody comprising at least one antigen binding domain of which binds to and inhibits activation of, an IL-33 receptor; or
 f) an antisense oligonucleotide.

In another embodiment, the IL-33 antagonist is
 a) an antibody, or antigen binding fragment of an antibody, that specifically binds to, and inhibits activation of, an IL-33 receptor;
 b) a soluble form of an IL-33 receptor that specifically binds to IL-33 and inhibits IL-33 from binding to the IL-33 receptor;
 c) an antisense nucleic acid that specifically inhibits synthesis of IL-33;
 d) a siRNA that specifically inhibits synthesis of IL-33;
 e) a small molecule that specifically inhibits the activity of IL-33; or
 f) a bispecific antibody comprising at least one antigen binding domain of which binds to and inhibits activation of, an IL-33 receptor.

In another embodiment, the IL-33 antagonist is a siRNA that specifically inhibits synthesis of ST2.

In one embodiment, the IL-33 antagonist is an antibody selected from the group consisting of chimeric antibodies, humanized antibodies, human antibodies, and antigen binding fragments of chimeric humanized and human antibodies. In another embodiment, the IL-33 antagonist is a soluble ST2 polypeptide, a soluble IL-1RAP protein or ANB020.

In one embodiment, the IL-33 antagonist is a bispecific antibody selected from the group consisting of
 i) asymmetric IgG-like bispecific antibodies;
 ii) symmetric IgG-like bispecific antibodies;
 iii) IgG fusion bispecific antibodies;
 iv) Fc fusion bispecific antibodies;
 v) Fab fusion bispecific antibodies;
 vi) ScFv- or diabody-based bispecific antibodies; and
 vii) IgG/Non-IgG fusion bispecific antibodies.

In one embodiment, the IL-33 antagonist is a RNA interference (RNAi) antagonist. In another embodiment, the IL-33 antagonist is:
 a. a small interfering RNA (siRNA);
 b. a short hairpin RNA (shRNA); or
 c. a siRNA that specifically inhibits synthesis of IL-33.

In another embodiment, the RNAi antagonist, the siRNA or the shRNA is directed to and targeting the IL-33 receptor ST2.

In a further embodiment, the IL-33 antagonist is administered orally, intralesionally, by intravenous therapy or by subcutaneous, intramuscular, intraarterial, intravenous, intracavitary, intracranial or intraperitoneal injection. In another embodiment, the IL-33 antagonist is administered by intravenous injection. In another embodiment, the IL-33 antagonist is administered orally.

In one embodiment, the IL-33 antagonist is injected directly into the affected tissue. In another embodiment, the IL-33 antagonist is injected to a site of maximal cellularity or maximal inflammation.

In one embodiment, the IL-33 antagonist is administered daily. In another embodiment, the IL-33 antagonist is administered weekly. In a further embodiment, the IL-33 antagonist is administered monthly. In a further embodiment, the IL-33 antagonist is administered once every three months, once every 6 months, or once every 12 months.

In one embodiment, the effective amount of the IL-33 antagonist is an amount between about 0.1 mg and about 500 mg.

In one embodiment, the method further comprises co-administering a TNF-α antagonist.

In one embodiment, the administration of the IL-33 antagonist precedes the administration of the TNF-α antagonist. In another embodiment, the patient is receiving the IL-33 antagonist prior to initiating administering the TNF-α antagonist and continues to receive the IL-33 antagonist after administration of the TNF-α antagonist is initiated.

In one embodiment, the administration of the TNF-α antagonist precedes the administration of the IL-33 antagonist. In another embodiment, the patient is receiving the TNF-α antagonist prior to initiating administering the IL-33 antagonist and continues to receive the IL-33 antagonist after administration of the TNF-α antagonist is initiated.

In an embodiment, the TNF-α antagonist, is a RNA interference (RNAi) antagonist. In another embodiment, the TNF-α antagonist is: (a) a small interfering RNA (siRNA); (b) a short hairpin RNA (shRNA); or (c) a siRNA that specifically inhibits synthesis of TNFR1 and/or TNFR2. In a further embodiment, the RNAi antagonist, the siRNA or the shRNA is directed to and targeting TNFR1 and/or TNFR2. In another embodiment, the siRNA is directed to and targeting the TNF receptor 2.

In one embodiment, the TNF-α antagonist is administered in an amount between about 0.05 and about 5.0 times the clinical dose of the TNF-α antagonist typically administered to a patient with rheumatoid arthritis. In another embodiment, the amount of the TNF-α antagonist is between about 5 mg and about 300 mg.

In one embodiment, the TNF-α antagonist is one or more of infliximab, adalimumab, certolizumab pegol, golimumab or etanercept.

In one embodiment, the TNF-α antagonist is golimumab and the amount of golimumab administered is between about 1 mg and about 90 mg.

In one embodiment, the TNF-α antagonist is adalimumab and the amount of adalimumab administered is between about 5 mg and about 100 mg.

In one embodiment, the TNF-α antagonist is certolizumab pegol and the amount of certolizumab pegol administered is between about 50 mg and about 200 mg.

In one embodiment, the TNF-α antagonist is infliximab and the amount of infliximab administered is between about 50 mg and about 300 mg.

In one embodiment, the TNF-α antagonist is etanercept and the amount of etanercept administered is between about 5 mg and about 50 mg.

In another embodiment, the TNF-α antagonist is a TNF receptor 2 (TNFR2) antagonist. In a further embodiment, the TNF-α antagonist is an antisense oligonucleotide. In an additional embodiment, the TNF-α antagonist is a RNA interference (RNAi) antagonist. In one embodiment, the TNF-α antagonist is: a) a siRNA; or b) a shRNA.

In one embodiment, the method further comprises co-administering a GM-CSF antagonist.

In one embodiment, the administration of the IL-33 antagonist precedes the administration of the GM-CSF antagonist. In another embodiment, the patient is receiving the IL-33 antagonist prior to initiating administering the GM-CSF antagonist and continues to receive the IL-33 antagonist after administration of the GM-CSF antagonist is initiated.

In one embodiment, the administration of the GM-CSF antagonist precedes the administration of the IL-33 antagonist. In another embodiment, the patient is receiving the GM-CSF antagonist prior to initiating administering the IL-33 antagonist and continues to receive the IL-33 antagonist after administration of the GM-CSF antagonist is initiated.

In one embodiment, the method further comprises co-administering one or more of an IL-17 antagonist, an IL-21 antagonist or an IL-23 antagonist.

In one embodiment, the administration of the IL-33 antagonist precedes the administration of the one or more of the IL-17 antagonist, the IL-21 antagonist, or the IL-23 antagonist. In another embodiment, the patient is receiving the IL-33 antagonist prior to initiating administering the one or more of the IL-17 antagonist, the IL-21 antagonist, or the IL-23 antagonist and continues to receive the IL-33 antagonist after administration of the one or more of the IL-17 antagonist, the IL-21 antagonist, or the IL-23 antagonist is initiated.

In one embodiment, the administration of the one or more of the IL-17 antagonist, the IL-21 antagonist, or the IL-23 antagonist precedes the administration of the IL-33 antagonist. In another embodiment, the patient is receiving the one or more of the IL-17 antagonist, the IL-21 antagonist, or the IL-23 antagonist prior to initiating administering the IL-33 antagonist and continues to receive the IL-33 antagonist after administration of the one or more of the IL-17 antagonist, the IL-21 antagonist, or the IL-23 antagonist is initiated.

In one embodiment, the amount of the one or more of the IL-17 antagonist, the IL-21 antagonist, or the IL-23 antagonist is between about 10 mg and about 300 mg.

In one embodiment, the method further comprises administering of a therapeutically, prophylactically or progression-inhibiting amount of a DAMP antagonist and/or an AGE inhibitor to the patient.

In one embodiment, a DAMP antagonist is administered and the DAMP antagonist is an Alarmin antagonist.

In one embodiment, the Alarmin antagonist is one or more of an antagonist of HMGB1, an antagonist of S100A8, an antagonist of S100A9, an antagonist of S100A8/9, and a heat shock protein.

In an embodiment, the methods of treatment of the present invention results in alleviation of a symptom of Dupuytren's disease, frozen shoulder (adhesive capsulitis), periarticular fibrosis, keloid or hypertrophic scars, endometriosis, abdominal adhesions, perineural fibrosis, Ledderhose disease, Peyronie's disease, peritendinous adhesions, or periarticular fibrosis. In another embodiment, the method of treatment results in improvement of the patient's quality of life or general health status.

In an embodiment, a ST2 antagonist is used instead of an IL-33 antagonist.

The antagonists of the present invention may be administered by injection together using a twin barreled syringe or at intervals separated by minutes to days. The antagonists may also be administered in a single syringe needle with the use of bispecific antibodies.

In an embodiment, the methods of the present invention further comprise co-administering one or more or human matrix metalloproteinases or collagenase *Clostridium histolyticum* (Xiaflex®). The human matrix metalloproteinase can be the native enzyme or modified to restrict activity, for example calcium dependent.

The subject invention also provides a method of treating a patient suffering from a localized fibrotic condition which comprises administering to the patient an amount of a TNF receptor 2 (TNFR2) antagonist effective to treat the patient.

In one embodiment, the localized fibrotic condition is selected from the group consisting of Dupuytren's disease, frozen shoulder (adhesive capsulitis), periarticular fibrosis, keloid or hypertrophic scars, endometriosis, abdominal adhesions, perineural fibrosis, Ledderhose disease, Peyronie's disease, peritendinous adhesions, and periarticular fibrosis. In a further embodiment, the localized fibrotic condition is selected from the group consisting of Dupuytren's disease, frozen shoulder (adhesive capsulitis), periarticular fibrosis, keloid or hypertrophic scars, endometriosis, abdominal adhesions, and Perineural fibrosis. In another embodiment, the localized fibrotic condition is Dupuytren's disease.

In another embodiment, the localized fibrotic condition is early disease state Dupuytren's disease. In another embodiment, the localized fibrotic condition is established disease state Dupuytren's disease. In another embodiment, the localized fibrotic condition is frozen shoulder (adhesive capsulitis). In another embodiment, the localized fibrotic condition is periarticular fibrosis. In another embodiment, the localized fibrotic condition is keloid or hypertrophic scars. In another embodiment, the localized fibrotic condition is Ledderhose disease. In another embodiment, the localized fibrotic condition is Peyronie's disease. In another embodiment, the localized fibrotic condition is endometriosis. In another embodiment, the localized fibrotic condition is abdominal adhesions. In another embodiment, the localized fibrotic condition is perineural fibrosis. In another embodiment, the localized fibrotic condition is peritendinous adhesions. In another embodiment, the localized fibrotic condition is periarticular fibrosis.

The invention additionally provides a method of treating a patient suffering from liver fibrosis or lung fibrosis which comprises administering to the patient an amount of a TNFR2 antagonist effective to treat the patient.

In another embodiment, the TNFR2 antagonist is
a) an antibody, or antigen binding fragment of an antibody, that specifically binds to, and inhibits activation of, an TNFR2;
b) a soluble form of an TNFR2 that specifically binds to TNFR2 and inhibits TNFR2 from binding to the TNFR2;
c) an antisense nucleic acid that specifically inhibits synthesis of TNFR2;
d) a siRNA that specifically inhibits synthesis of TNFR2;
e) a small molecule that specifically inhibits the activity of TNFR2; or
f) a bispecific antibody comprising at least one antigen binding domain of which binds to and inhibits activation of, an TNFR2; or
g) an antisense oligonucleotide.

In one embodiment, the TNFR2 antagonist is an antibody selected from the group consisting of chimeric antibodies, humanized antibodies, human antibodies, and antigen binding fragments of chimeric humanized and human antibodies.

In one embodiment, the TNFR2 antagonist is a bispecific antibody selected from the group consisting of
i) asymmetric IgG-like bispecific antibodies;
ii) symmetric IgG-like bispecific antibodies;
iii) IgG fusion bispecific antibodies;
iv) Fc fusion bispecific antibodies;
v) Fab fusion bispecific antibodies;
vi) ScFv- or diabody-based bispecific antibodies; and
vii) IgG/Non-IgG fusion bispecific antibodies.

In another embodiment, the TNFR2 antagonist is a RNA interference (RNAi) antagonist.

In a further embodiment, the TNFR2 antagonist is:
a. a small interfering RNA (siRNA);
b. a short hairpin RNA (shRNA); or
c. a siRNA that specifically inhibits synthesis of TNFR2.

In one embodiment, the TNFR2 antagonist is administered orally, intralesionally, by intravenous therapy or by subcutaneous, intramuscular, intraarterial, intravenous, intracavitary, intracranial, or intraperitoneal injection. In another embodiment, the TNFR2 antagonist is administered by intravenous injection. In a additional embodiment, the TNFR2 antagonist is administered orally.

In one embodiment, the TNFR2 antagonist is injected directly into the affected tissue. In another embodiment, the TNFR2 antagonist is injected to a site of maximal cellularity or maximal inflammation.

In one embodiment, the TNFR2 antagonist is administered daily. In another embodiment, the TNFR2 antagonist is administered weekly. In a further embodiment, the TNFR2 antagonist is administered monthly. In an additionally embodiment, the TNFR2 antagonist is administered once every three months, once every 6 months, or once every 12 months.

In one embodiment, the TNFR2 antagonist is administered in an amount between about 5 mg and about 300 mg.

In another embodiment, the method further comprises administering a therapeutically, prophylactically or progression-inhibiting amount of a DAMP antagonist and/or an AGE inhibitor to the patient. In one embodiment, a DAMP antagonist is administered and the DAMP antagonist is an Alarmin antagonist.

In an additional embodiment, the Alarmin antagonist is one or more of an antagonist of HMGB1, an antagonist of S100A8, an antagonist of S100A9, an antagonist of S100A8/9, and a heat shock protein.

For the foregoing embodiments, each embodiment disclosed herein is contemplated as being applicable to each of the other disclosed embodiments. In addition, the elements recited in the packaging and pharmaceutical composition embodiments can be used in the method and use embodiments described herein.

Pharmaceutically Acceptable Salts

The active compounds for use according to the invention may be provided in any form suitable for the intended administration. Suitable forms of the pre- or prodrug or functionally active protein produced as an active pharmaceutical ingredient, through recombinant DNA technology, include pharmaceutically (i.e. physiologically) acceptable salts, formulations, and excipients, known to those skilled in the art, for the compound(s) of the invention.

The antagonists of the present invention may act by RNA interference. Additionally, the antagonists of the present invention include, but are not limited to, siRNAs or shRNAs.

RNA interference (RNAi) refers to a process in which RNA molecules modulate and/or silence gene expression (Lagana 2015). Small interfering RNAs (siRNA) are a class of double-stranded RNA molecules which have a variety of known effects, including interference with the expression of specific genes expression (Lagana 2015). Short hairpin RNA (shRNA) refers to sequences of RNA that make tight hairpin turns that can be used to silence gene expression (Paddison 2002).

In mammals, both genome-wide and subgenomic, focused libraries of synthetic siRNAs and shRNA expression constructs are widely used (Silva 2008; Luo 2009; Barbie 2009).

The RNAi process and the use of siRNAs and shRNAs are known in the art and may be found in the following publications which are hereby incorporated by reference: U.S. Patent Publication Nos. 20130330730A1 and 20060003915; U.S. Pat. Nos. 7,893,243, 8,735,064, 6,506,559, 8,420,391, 7,560,438, and 7,416,849; PCT International Publication Nos. WO 2004076629 WO 1999/32619, WO 2001/68836, WO 2001/77350, WO 2000/44895, WO 2002/055692 and WO 2002/055693; Rao 2010, and Kanasty 2013.

The RNA molecules of the present invention that act by RNAi may be administered directly or be expressed in vivo from a suitable construct. Additionally, the siRNA and shRNA of the present invention may also be administered directly or be expressed in vivo from a suitable construct.

The RNA molecules of the present invention involved in RNAi includes chemically modified RNA molecules. Likewise, the siRNAs of the present invention includes chemically modified siRNAs. Additionally, the shRNAs of the present invention includes chemically modified shRNAs. Examples of chemically modified RNA molecules, chemically modified siRNAs and chemically modified shRNAs include, but are not limited to, those listed in the following publications: U.S. Pat. Nos. 7,956,176, 8,541,385, 8,871,730, 8,618,277, and 9,181,551; Dar 2015, Gaglione 2010, Deleavey 2012, and Chiu 2003.

Terms

As used herein, and unless stated otherwise, each of the following terms shall have the definition set forth below.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a localized fibrotic condition. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, an "amount" of a compound as measured in milligrams refers to the milligrams of compound present in a preparation, regardless of the form of the preparation. An "amount of compound which is 90 mg" means the amount of the compound in a preparation is 90 mg, regardless of the form of the preparation. Thus, when in the form with a carrier, the weight of the carrier necessary to provide a dose of 90 mg compound would be greater than 90 mg due to the presence of the carrier.

As used herein, "about" in the context of a numerical value or range means ±10% of the numerical value or range recited or claimed.

As used herein, to "treat" or "treating" encompasses, e.g., inducing inhibition, regression, or stasis of the disorder and/or disease. As used herein, "inhibition" of disease progression or disease complication in a subject means preventing or reducing or reversing the disease progression and/or disease complication in the subject.

Any known IL-33 antagonist may be utilized in the implementation of this invention. The IL-33 antagonist ANB020 is a functional anti-IL-33 therapeutic antibody currently in development. ANB020 inhibits IL-33 cytokine function by blocking interaction with the IL-33 cytokine's receptor at low picomolar potency. The IL-33 antagonist may be a decoy receptor, such as soluble ST2 (sST2) (Kakkar, 2008). The IL-33 antagonist may also be a receptor (ST2/IL-1RAP) inhibitor. IL-33 antagonists may be administered at dosages between 0.001 mg/kg to 1 mg/kg.

Where the IL-33 antagonist comprises a bispecific (or bifunctional) antibody fragment or portion, the bispecific antibody or fragment thereof may comprise as one variable domain (e.g. antigen binding portion) an IL-33 antagonist and as the other variable domain (e.g. antigen binding portion) a second variable domain other than IL-33 antagonist. Optionally, the second variable domain may comprise a TNF-α antagonist, a GM-CSF antagonist, an IL-17 antagonist, an IL-21 antagonist or an IL-23 antagonist. A higher dose of IL-33 antagonist may be administered since the antibody or fragment thereof will be self-localising, minimizing systemic uptake and thus systemic side effects. Optionally, the second variable domain may comprise a DAMP antagonist (such as an antagonist for S100A8 and/or S100A9, e.g. as described in U.S. Pat. No. 7,553,488) or an AGE inhibitor (e.g. being variable domains of DAMP antagonist antibody or AGE inhibitor antibody). Methods for the production of bispecific (or bifunctional) antibodies, and bispecific (or bifunctional) antibody fragments are known in the art, which methods may be applied to the present purpose.

Any known TNF-α antagonist (or TNF antagonist) may be utilized in the implementation of the invention, a broad variety of which are known and disclosed in the art. The TNF-α antagonist is preferably a human TNF-α antagonist. Optionally, the TNF antagonist may be an antibody, such as a monoclonal antibody or fragment thereof; a chimeric monoclonal antibody (such as a human-murine chimeric monoclonal antibody); a fully human monoclonal antibody; a recombinant human monoclonal antibody; a humanized antibody fragment; a soluble TNF antagonist, including small molecule TNF blocking agents such as thalidomide or analogues thereof or PDE-IV inhibitors; a TNF receptor or a TNF receptor fusion protein, e.g. a soluble TNFR1 (p55) or TNFR2 (p75) TNF receptor or TNF receptor fusion protein. Optionally, the TNF antagonist is a functional fragment or fusion protein comprising a functional fragment of a monoclonal antibody, e.g. of the 15 types mentioned above, such as a Fab, F(ab')2, Fv and preferably Fab. Preferably a fragment is pegylated or encapsulated (e.g. for stability and/or sustained release). The TNF-α antagonist may also be a camelid antibody. As used herein, TNF-α antagonists include but are not limited to TNF receptor inhibitors.

Preferably, the TNF-α antagonist is selected from those which at administration (e.g. local administration, such as injection into: a clinical nodule or cord of Dupuytren's disease, a localized deposit endometriosis, the inflammatory nodule in adhesive capsulitis, hypertrophic scar, or keloid scar) cause administration-site irritation manifested as palpable local swelling, redness and pruritis in fewer than 40% of patients, preferably fewer than 20% and more preferably fewer than 10%.

The TNF-α antagonist may be selected, for example, from one or a combination of Infliximab, Adalimumab, Certolizumab pegol, Golimumab or Etanercept, or functional fragment thereof.

Any known GM-CSF (Granulocyte-macrophage colony-stimulating factor) antagonist may be utilized in the implementation of this invention. The GM-CSF antagonist may be: an antibody, or antigen binding fragment of an antibody, that specifically binds to, and inhibits activation of, an GM-CSF receptor; a soluble form of an GM-CSF receptor that specifically binds to GM-CSF and inhibits GM-CSF from binding to the GM-CSF receptor; an antisense nucleic acid that specifically inhibits synthesis of GM-CSF; a siRNA that specifically inhibits synthesis of GM-CSF; a small molecule that specifically inhibits the activity of GM-CSF; or a bispecific antibody comprising at least one antigen binding domain of which binds to and inhibits activation of, an GM-CSF receptor. The GM-CSF antagonist may be an antibody selected from the group consisting of chimeric antibodies, humanized antibodies, human antibodies, and antigen binding fragments of chimeric humanized and human antibodies. Examples of GM-CSF antagonists include, but are not limited to, E21R and E21K. Other examples of GM-CSF antagonists are described in U.S. Pat. No. 8,398,972, the contents of which are hereby incorporated by reference.

Any known IL-17 (Interleukin 17) antagonist may be utilized in the implementation of this invention. The IL-17 antagonist may be: an antibody, or antigen binding fragment of an antibody, that specifically binds to, and inhibits activation of, an IL-17 receptor; a soluble form of an IL-17 receptor that specifically binds to IL-17 and inhibits IL-17 from binding to the IL-17 receptor; an antisense nucleic acid that specifically inhibits synthesis of IL-17; a siRNA that specifically inhibits synthesis of IL-17; a small molecule that specifically inhibits the activity of IL-17; or a bispecific antibody comprising at least one antigen binding domain of which binds to and inhibits activation of, an IL-17 receptor. The IL-17 antagonist may be an antibody selected from the group consisting of chimeric antibodies, humanized antibodies, human antibodies, and antigen binding fragments of chimeric humanized and human antibodies. Examples of IL-17 antagonists include, but are not limited to, secukinumab, brodalumaband, and ixekizumab. Other examples of IL-17 antagonists are described in PCT International Publication Nos. WO2012045848A1 and WO2012059598A2, the contents of which are hereby incorporated by reference.

Any known IL-21 (Interleukin 21) antagonist may be utilized in the implementation of this invention. The IL-21 antagonist may be: an antibody, or antigen binding fragment of an antibody, that specifically binds to, and inhibits activation of, an IL-21 receptor; a soluble form of an IL-21 receptor that specifically binds to IL-21 and inhibits IL-21 from binding to the IL-21 receptor; an antisense nucleic acid that specifically inhibits synthesis of IL-21; a siRNA that specifically inhibits synthesis of IL-21; a small molecule that specifically inhibits the activity of IL-21; or a bispecific antibody comprising at least one antigen binding domain of which binds to and inhibits activation of, an IL-21 receptor. The IL-21 antagonist may be an antibody selected from the group consisting of chimeric antibodies, humanized antibodies, human antibodies, and antigen binding fragments of chimeric humanized and human antibodies. Examples of IL-21 antagonists are described in U.S. Pat. No. 7,923,539, and PCT International Publication Nos. WO 2007/114861 and WO 2003040313 A2, the contents of which are hereby incorporated by reference.

Any known IL-23 (Interleukin 23) antagonist may be utilized in the implementation of this invention. The IL-23 antagonist may be: an antibody, or antigen binding fragment of an antibody, that specifically binds to, and inhibits activation of, an IL-23 receptor; a soluble form of an IL-23 receptor that specifically binds to IL-23 and inhibits IL-23 from binding to the IL-23 receptor; an antisense nucleic acid that specifically inhibits synthesis of IL-23; a siRNA that specifically inhibits synthesis of IL-23; a small molecule that specifically inhibits the activity of IL-23; or a bispecific antibody comprising at least one antigen binding domain of which binds to and inhibits activation of, an IL-23 receptor. The IL-23 antagonist may be an antibody selected from the group consisting of chimeric antibodies, humanized antibodies, human antibodies, and antigen binding fragments of chimeric humanized and human antibodies. Examples of IL-23 antagonists include, but are not limited to, ustekinumab and briakinumab. Other examples of IL-23 antagonists are described in PCT International Publication No. WO 2007147019 the contents of which are hereby incorporated by reference.

An RNA interference (RNAi) antagonist is an RNA molecule that modulates or inhibits gene expression.

By early disease, early disease stage, or early disease state it is meant that indications of disease are present, e.g. histological markers or more particularly clinical nodules in tissue, but in the absence of, for example, palpable cord or significant contracture. By early Dupuytren's disease, early disease stage Dupuytren's disease or early disease state Dupuytren's disease, it is meant that indications of Dupuytren's disease are present, for example histological markers or more particularly clinical nodules in palmar and/or digital tissue, and a flexion deformity of less than or equal to 30 degrees at any joint in the digit.

By established disease stage or established disease state, it is meant that clinical nodules are present, palpable cord is present and contracture is evident. By established disease stage Dupuytren's disease, it is meant that clinical nodules are present on the palm and digits of the hand and a flexion deformity of greater than 30 degrees at any joint in the digit.

Varying histological stages of Dupuytren's disease have been categorised in the literature, most succinctly by Rombouts, 1989 and later authors, into three distinct stages: 1) a proliferative stage with high cellularity and the presence of mitotic figures; 2) a fibrocellular stage characterised by high cellularity but no mitotic figures and the presence of reticulin network; and 3) a fibrous stage with few cells separated by broad bundles of collagen fibres. Stage 1) disease is believed to correlate with early disease stage as discussed above (i.e. presence of nodules but no contracture) and Dupuytren's stages 2) and 3) is believed to correlate with our Established Disease Stage (characterized by digital contracture). During early and early established disease stages, active myofibroblasts are collected in the established nodules and cords, especially in relation to the MCP and PIP joints and these drive the progression of flexion contractures of the digit.

In certain claims, the invention claims the amount of the TNF antagonist as a multiple of the clinical dose administered for Rheumatoid Arthritis. For example, if a claim states the TNF-α antagonist is administered in an amount between about 0.05 and about 5.0 times the clinical dose of the TNF-α antagonist typically administered to a patient with rheumatoid arthritis, and the clinical dose administered for Rheumatoid Arthritis for that particulate TNF-α antagonist is 100 mg, then the dose of the TNF-α antagonist for the claimed method is between 5 mg and 500 mg.

The antagonists of the present invention may be injected directly into the affected tissue. The antagonists of the present invention may be injected to a site of maximal cellularity or maximal inflammation.

The antagonist may be administered by intra articular injection, peri articular injection, systemic injection (IV), or subcutaneous injection (SC) to a patient with peri-articular fibrosis, by intra articular injection, peri articular injection, systemic injection (IV) or subcutaneous injection (SC) to a patient with frozen shoulder, by intralesional injection, systemic injection (IV) or subcutaneous injection (SC) to a patient with cutaneous scarring (keloid & hypertrophic), by intra-peritoneal injections, systemic injection (IV), or subcutaneous injection (SC) to a patient with abdominal adhesions or by intralesional injection, intra-peritoneal injections, systemic injection (IV), or by subcutaneous injection (SC) to a patient with endometriosis.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

By systematically unraveling the signaling pathways, TNF was identified as a novel therapeutic target to down regulate myofibroblasts, the cells responsible for matrix deposition and contraction in Dupuytren's disease (DD) (Verjee, 2013). Anti-TNF drugs have been used for more than 10 years to treat inflammatory conditions including rheumatoid arthritis, psoriatic arthritis, juvenile arthritis, Crohn's colitis, ankylosing spondylitis and psoriasis. Although these drugs can reduce the disease-associated inflammation, they do not reverse the underlying mechanisms that drive inflammation. As a result, they have to be administered at regular intervals. Whilst TNF inhibition could be used clinically to treat early Dupuytren's disease or to prevent recurrence, it will also likely need to be injected repeatedly on a regular basis, as for rheumatoid arthritis (Taylor, 2009). A survey showed a high acceptance rate for one injection per year but this fell sharply when frequency of injection was increased to 3 per year (Table 1).

TABLE 1

Summary of responses to questionnaire regarding acceptability of injection therapy that would prevent the progression of disease and hence avoid the necessity of future surgery.

| Extremely or very likely accept: | Patients with early Dupuytren's disease (n = 14) | Patients post surgery for Dupuytren's disease (n = 17) | Combined (n = 31) |
|---|---|---|---|
| 1 injection/yr for lifetime | 93% | 94% | 94% |
| 3 injections/yr for lifetime | 57% | 71% | 65% |

Targeting the pathway that drives chronicity will likely reduce the frequency of anti-TNF injections necessary to control progression of the disease. IL-33 is likely one of the important factors responsible for the chronic inflammation seen in Dupuytren's disease and related disorders such as frozen shoulder and Peyronie's disease.

IL-33 is the most recently described member of the IL-1 family of cytokines and plays an important role in fibrotic disorders in a variety of tissues (Palmer, 2011). Its expression is limited to fibroblasts, myofibroblasts, smooth muscle, epithelial and dendritic cells (Schmitz, 2005) and is markedly increased by pro-inflammatory cytokines (Xu, 2008). It has been shown to play a key role in fibrotic disorders in a variety of tissues, including the skin (Rankin, 2010) and gut (Sponheim, 2010). In active lesions of ulcerative colitis, myofibroblasts are the major source of IL-33 (Kobori, 2010). IL-33 can activate inflammatory cells, including mast cells and macrophages via the ST2L/IL1RAP receptor to secrete pro-inflammatory cytokines, in particular TNF, and systemic anti-TNF therapy can reduce circulating IL-33 levels (Pastorelli, 2010). Fibroblasts also secrete IL-33 in response to mechanical strain in vitro (Kunisch, 2012). This is particularly pertinent as strain is crucial to the development and persistence of myofibroblasts; on loss of tension, they disassemble their α-SMA within hours (Hinz, 2001). However, the precise role of IL-33 in driving musculoskeletal and other localized fibrotic diseases such as endometriosis, abdominal adhesions, adhesive capsulitis, hypertrophic scars or keloid scars, Ledderhose disease and Peyronie's disease is not clear.

Whilst best known as effector cells in allergic responses, mast cells are now recognised as important physiological regulators of the innate and adaptive immune response, smooth muscle contraction and wound healing (Bischoff, 2007). Mast cells constitutively express the IL-33 receptor ST2/IL1-RAP, and on exposure to IL-33, secrete pro-inflammatory cytokines including TNF without degranulation (Moulin, 2007). Whilst the differentiation and function of myofibroblasts can be regulated by mast cells (Gailit, 2001), the precise contribution of mast cell derived pro-inflammatory cytokines in driving myofibroblast formation in Dupuytren's disease disease and other localized fibrotic disorders has not been established.

Dupuytren's tissue has been shown to be composed mainly of myofibroblasts and about 7% of all cells comprise macrophages, predominantly of the M1 phenotype. Significant numbers of mast cells have been found in Dupuytren's disease tissue (FIG. 1).

Figure 1:
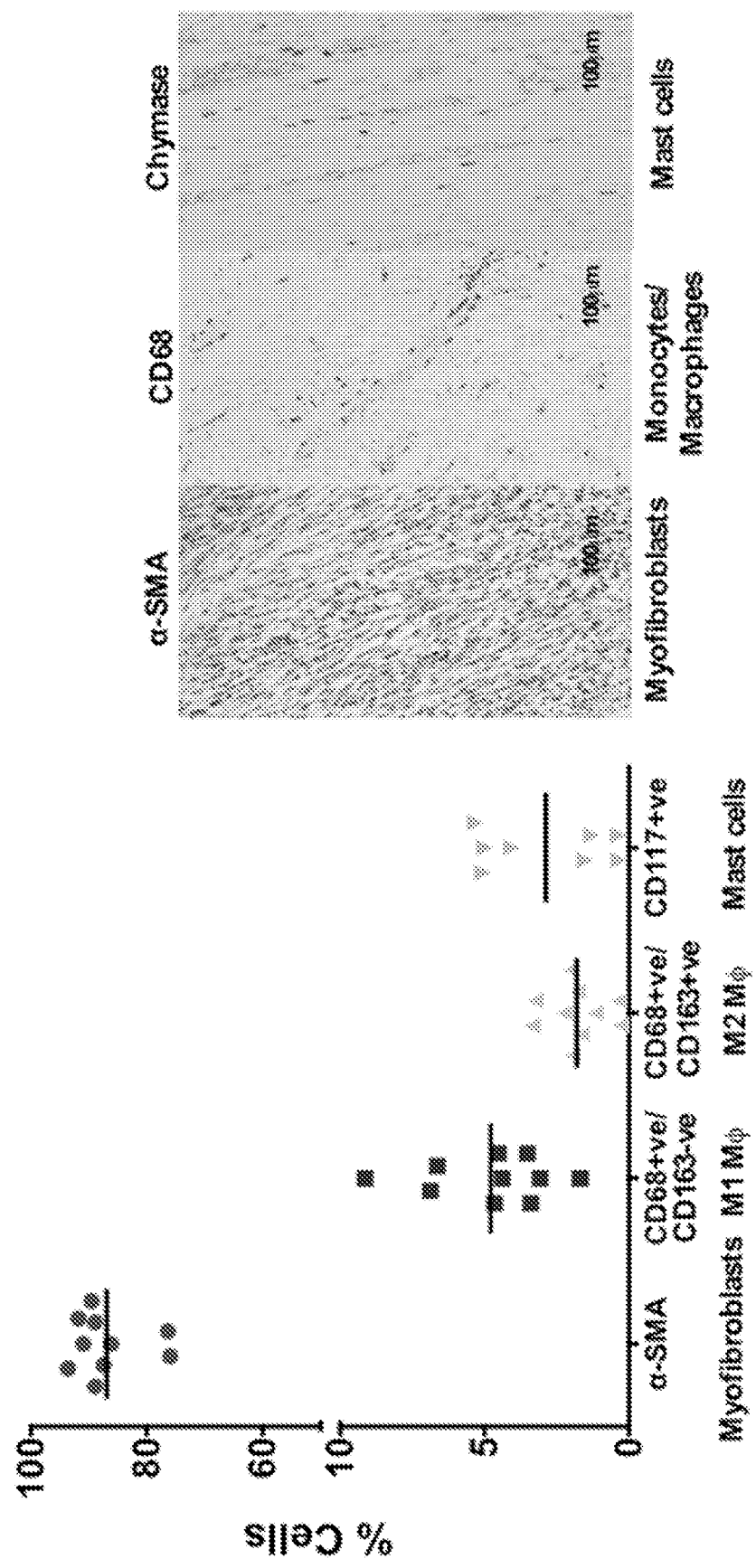
FIG. 1: Immune cells are present in Dupuytren's myofibroblast-rich tissue and release pro-inflammatory cytokines. (A) Flow cytometric analysis of cells isolated from freshly disaggregated Dupuytren's tissue. Intracellular α-SMA-positive (myofibroblasts; mean±SD: 87±6.1%), cell surface CD68-positive/CD163-negative (classically activated M1 macrophages; mean±SD: 4.8±2.2%), CD68-positive/CD163-positive (alternatively activated M2 macrophages; mean±SD: 1.8±1.0%) and CD117-positive (mast cells; mean±SD: 2.8±2.6% cells were quantified.) (B) Serial histological sections of Dupuytren's tissue stained for α-SMA+ (myofibroblasts), CD68+(monocytes) and chymase+(mast cells) (Scale bar, 100 μm.)
Figure 4A:
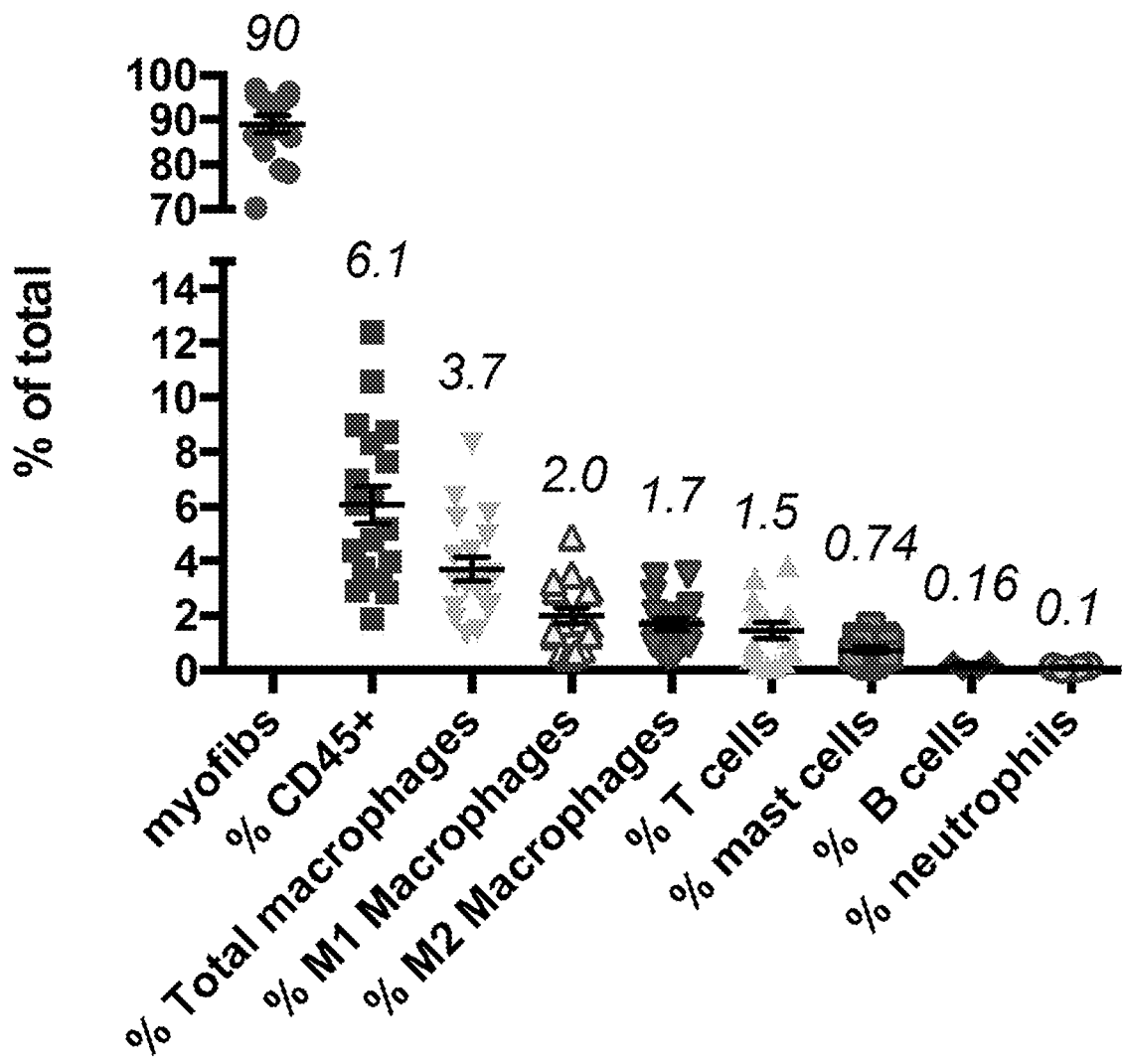
FIG. 4A-4C: Immune cells are present in Dupuytren's nodules and secrete cytokines.
Figure 4B:
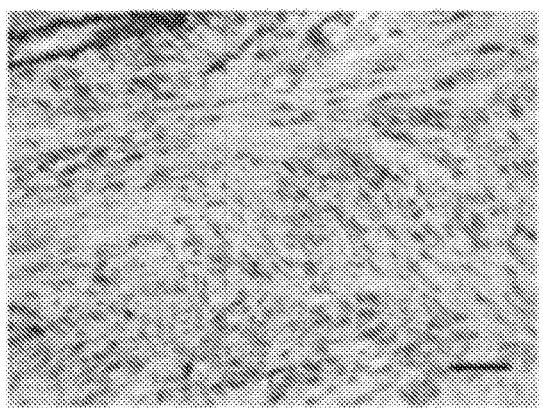
Figure 4B:
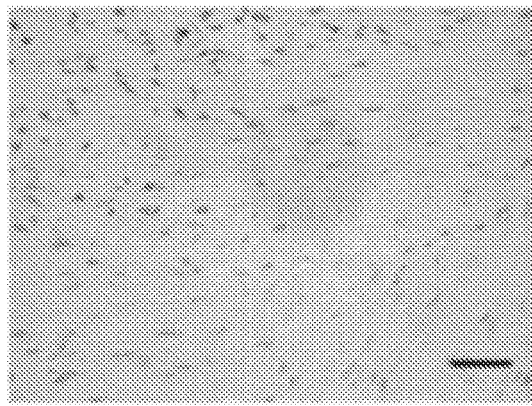
Figure 4B:
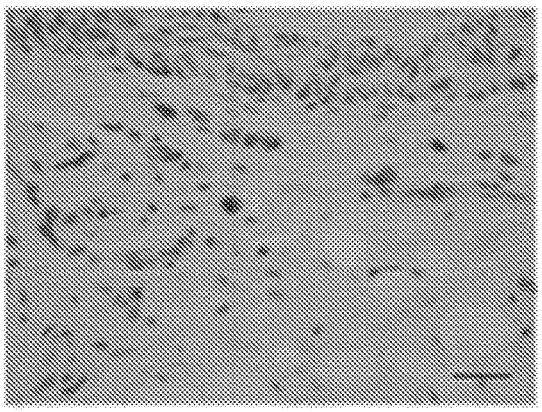
Figure 4B:
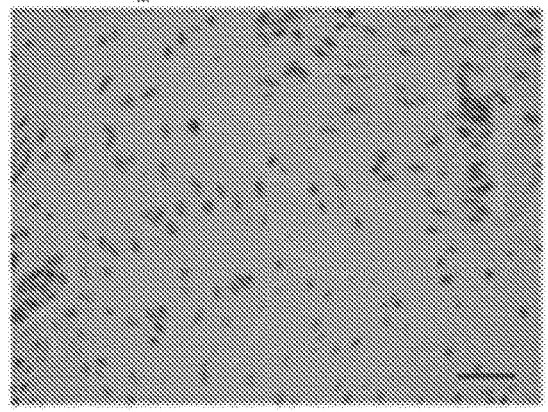
Figure 4B:
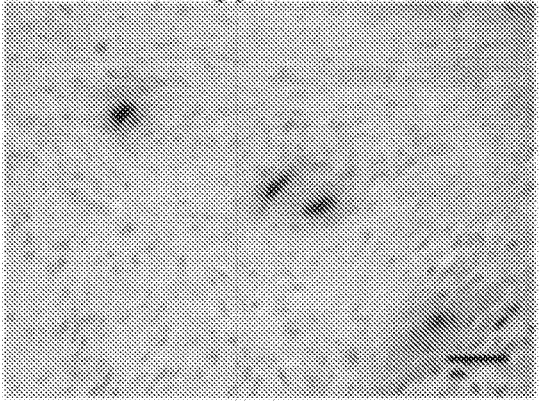
Figure 4B:
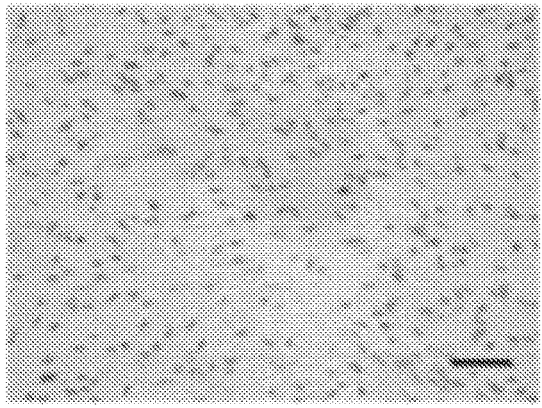
Figure 4C:
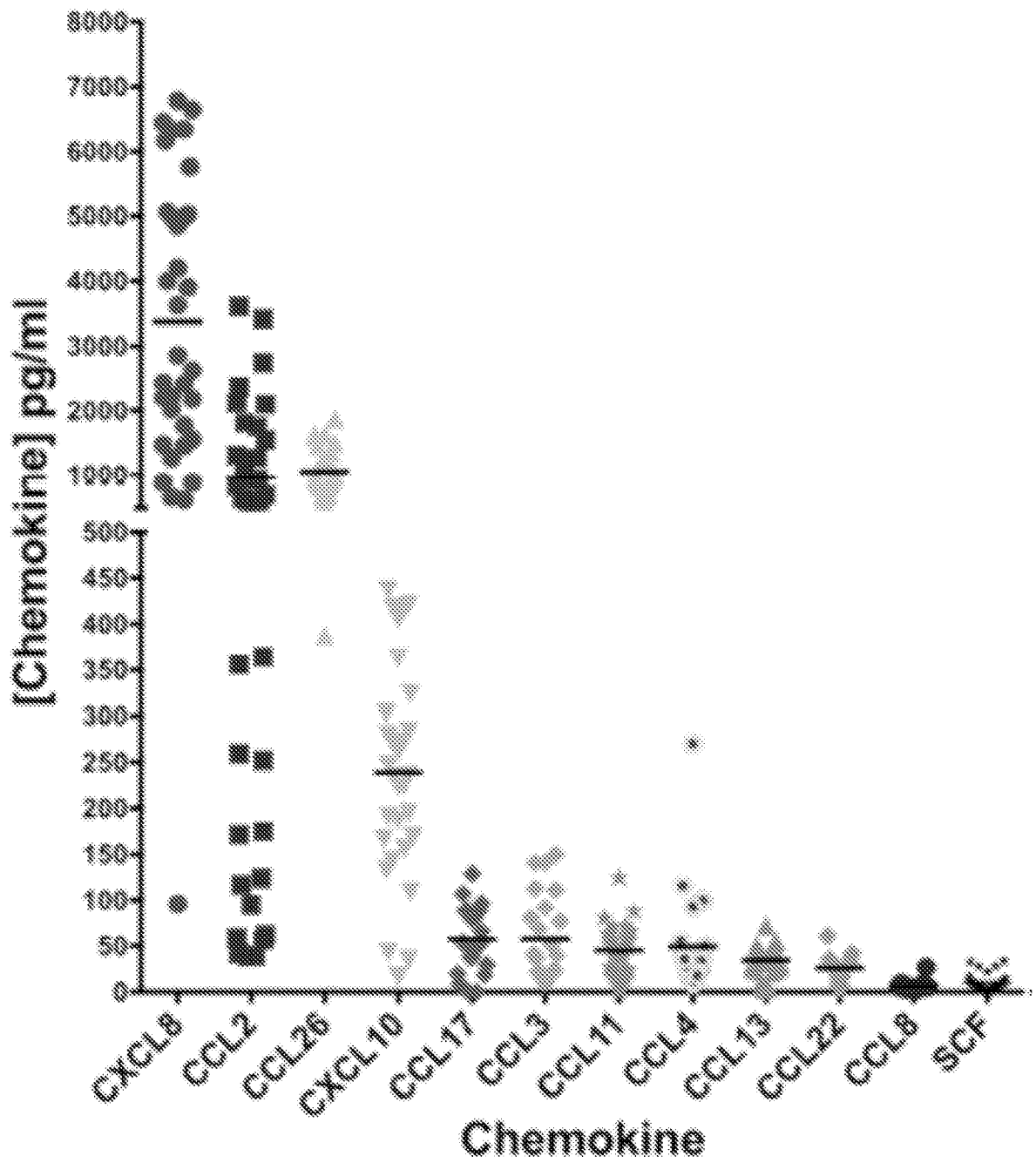

Analysis of supernatants from freshly disaggregated Dupuytren's tissue for a panel of cytokines and chemokines using Mesoscale Discovery (MSD) and detected IL-6 (FIG. 1), CCL2, CXCL8 (IL-8), CXCL10, and CCL26 (FIG. 4C) are presented in FIGS. 1 and 4C. The latter three are known chemokines for mast cells, which also require IL-6 as a growth factor. Elevated CXCL10 and CCL2 levels are consistent with the preponderance of classically activated M1 macrophages found in the Dupuytren's tissue (FIG. 1). These data suggest that macrophages and mast cells may be attracted to the Dupuytren's tissue by locally produced chemokines.

IL-33 was detected in the supernatant of freshly disaggregated Dupuytren's tissue (13.07±10.32 pg/ml) as shown in FIG. 1.

The best characterized human mast cell lines are LAD2, HMC1.1 and HMC1.2. Exposure of all three cell lines to recombinant human IL-33 (rhIL-33) resulted in a dose dependent secretion of TNF (FIG. 6D). Concentrations of IL-33 of the order released by freshly disaggregated tissue (10 pg/ml) led to TNF production at concentrations similar to those secreted ex vivo by freshly disaggregated cells from Dupuytren's nodules (Verjee, 2013).

Figure 2:
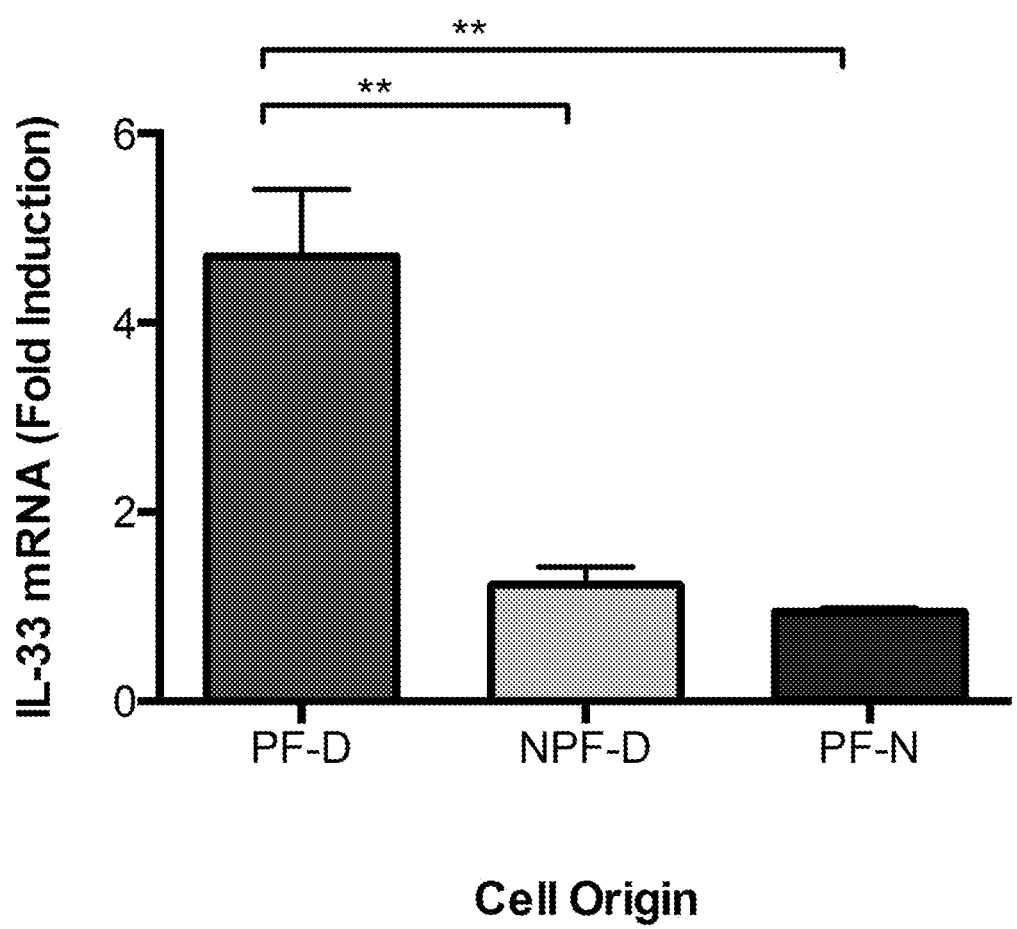
FIG. 2: TNF selectively induces IL-33 mRNA expression in palmar dermal fibroblasts. 0.1 ng/ml rhTNF stimulation for 24 h selectively induced IL-33 mRNA expression in dermal palmar fibroblasts (PF-D) at hours. rhTNF did not have any effect on non-palmar dermal fibroblasts from Dupuytren's patients (NPF-D), or palmar dermal fibroblasts from normal individuals without Dupuytren's disease (PF-N). n=5 patients for all cell types. **P<0.001

Only palmar dermal fibroblasts (PF-D) from patients with Dupuytren's disease expressed IL-33 on exposure to TNF (FIG. 2) while TGF-β1 indiscriminately induced expression of IL-33 in both palmar and non-palmar dermal fibroblasts (NPF-D) from these patients and in dermal fibroblasts from normal non-Dupuytren's controls (PF-N).

Figure 3:
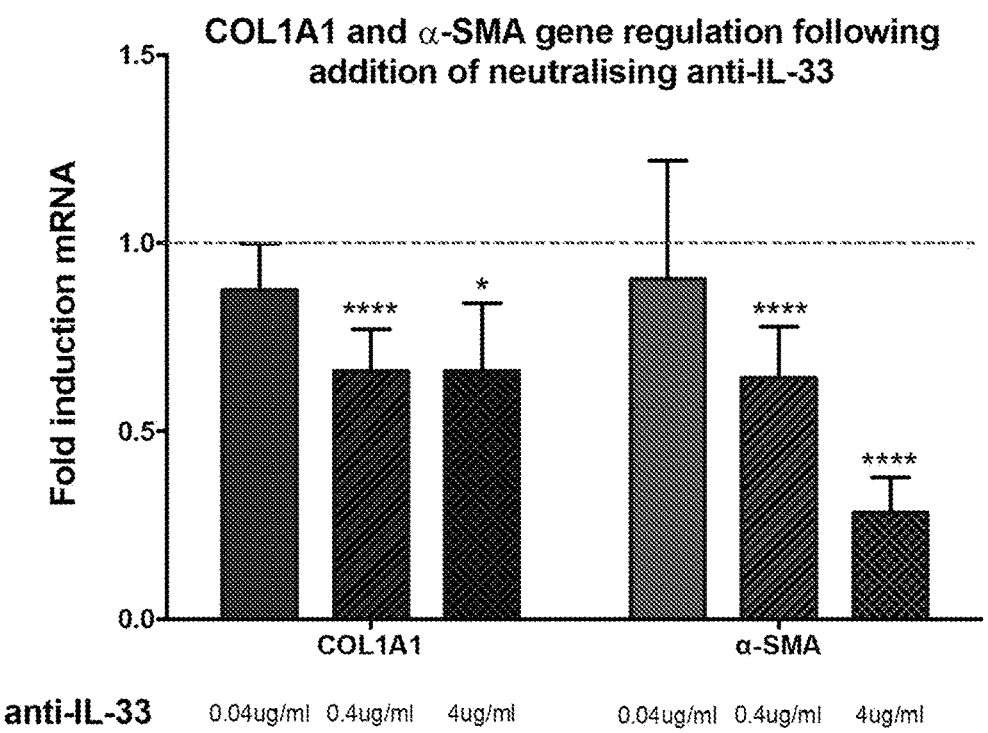
FIG. 3: Myofibroblasts from patients with Dupuytren's disease (MF-D) respond to neutralizing anti-IL-33 in a dose-dependent manner. (A) Anti-IL-33 downregulates relative COL1A1 and α-SMA mRNA expression; (B) Anti-IL-33 downregulates the relative expression of TNF receptor 1 (TNFR1) and TNF receptor 2 (TNFR2) (C) Anti-IL-33 downregulates relative expression of mRNA of IL-33 and its cell surface receptor ST2L. All values were normalized to fold change compared to untreated MF-D. n=3 for 0.04 ug/ml and 4 ug/ml anti-IL-33 and n=6 for 0.4 ug/ml anti-IL-33. IgG isotype control for anti-IL-33 showed no effect in the relative expression of the genes at the corresponding doses tested. Data expressed as mean±SEM. *P<0.05, P<0.01, *P<0.001,****P<0.0001. Methods: $1\times10^6$ cells were cultured in monolayer and treated with rhTNF (300-01A, Peprotech), neutralizing anti-TNF (MAB2101, R&D), neutralizing anti-TNF receptor 1 (MAB625, R&D), neutralizing anti-TNF receptor 2 (MAB726, R&D), anti-TNF/TNF receptors isotype control (MAB002, R&D), neutralizing anti-IL-33 (500-P261, Peprotech) or isotype control (500-P00, Peprotech). The total RNA was extracted from each sample using a QIAshredder, followed by QIAamp RNeasy Mini Kit (74104, Qiagen) with on-column RNase-Free DNase set (79254, Qiagen) according to the manufacturer's instructions. RNA was eluted in 30 μl RNase-free water provided and quantified using a NanoDrop ND-1000 spectrophotometer (NanoDrop Technologies), ensuring a 260/230 and 280/260 ratios >2.0. For real-time reverse transcription PCR, Inventoried TagMang Gene expression Assays were used for α-SMA (Hs00426835-g1), COL1A1 (Hs00164004-m1), TNFR1 (Hs01042313-m1) and TNFR2 (Hs00961749-m1), IL-33(Hs00369211 m1) and ST2 (Hs00545033 m1) (Applied Biosystems) with Reverse Transcriptase qPCRTh Mastermix No ROX (RT-QPRT-032XNR, Eurogentec). A total of 10 μl of reaction mixture containing 2 μl of RNA at 50 ng/ml, 5 μl of 2× buffer, 0.5 μl Taqman probe, 0.05 μl of Reverse Transcriptase enzyme with RNase inhibitors and 2.45 μl RNase free water were added to each well of a 384 well plate. Samples were run on the ABI VAii 7™ Real-Time PCR System (Applied Biosystems). Expression was normalized to GAPDH (Hs02758991-g1, Applied Biosystems) and compared to the level of gene expression in baseline respective cell types, which were assigned the value of 1 using delta delta CT analysis performed with SDS software (Applied Biosystems).
Figure 3:
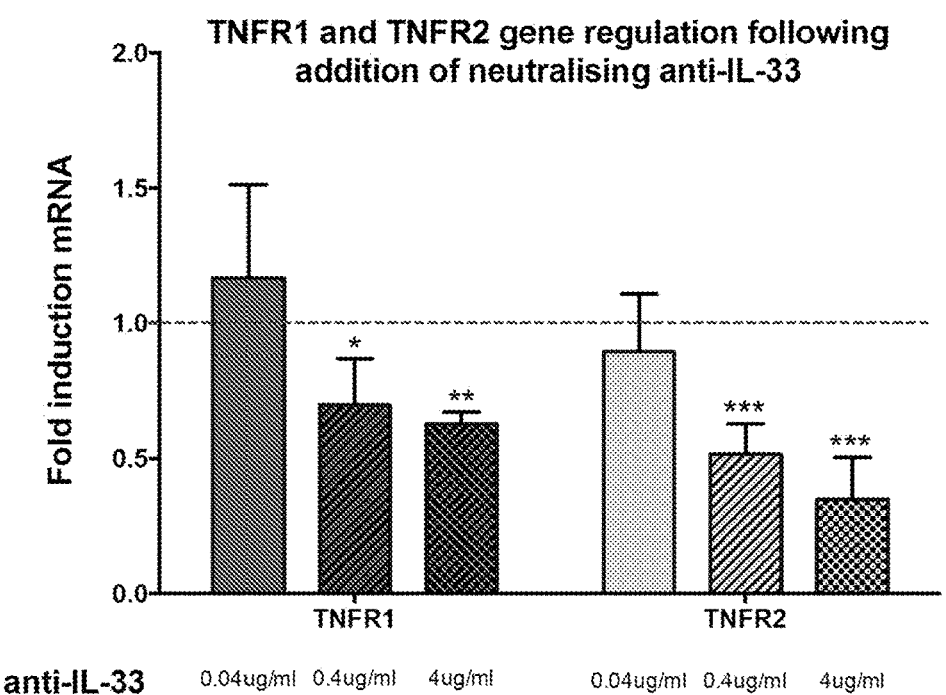
Figure 3:
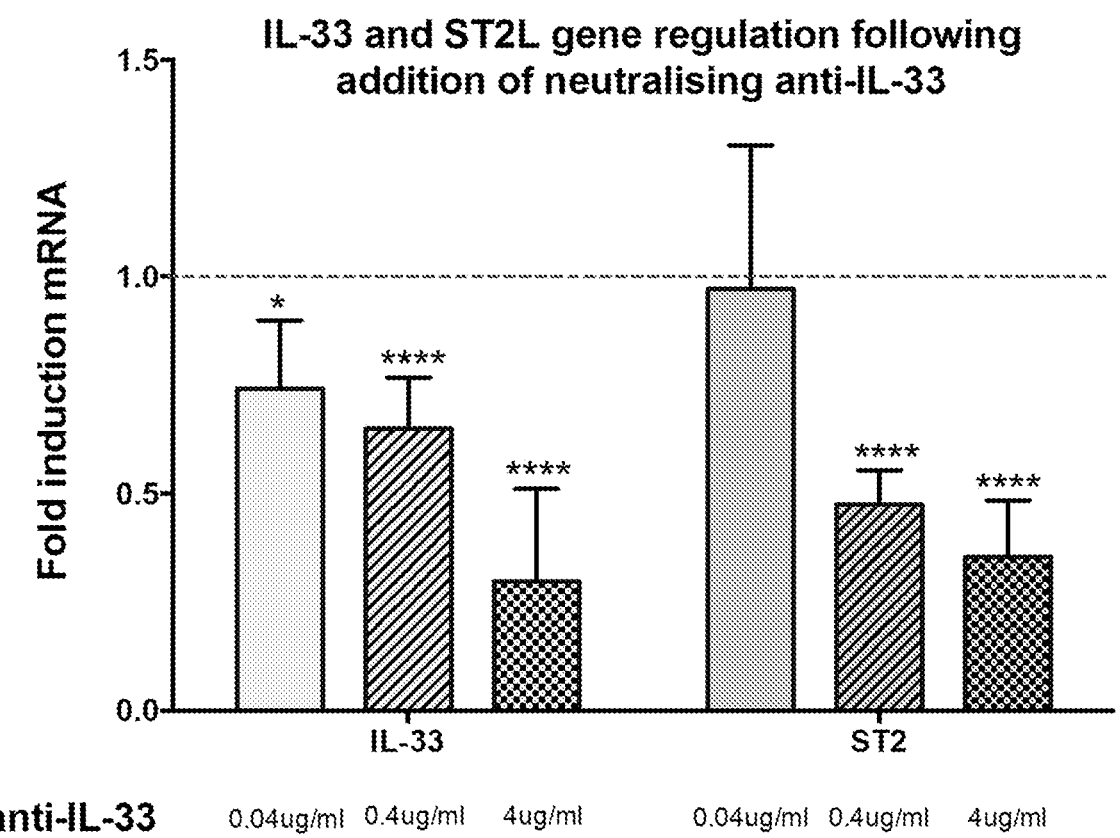

Treatment with anti-IL-33 resulted in a downregulation of the myofibroblasts phenotype in a dose-dependent manner (FIG. 3A). Inhibition of IL-33 also resulted in reduction of IL-33 and ST2 (a receptor for IL-33) expression by myofibroblasts, again in a dose-dependent manner (FIG. 3C). The interaction between the IL-33 and TNF pathways was confirmed as anti-IL-33 resulted in reduced expression of the receptors for TNF, TNFR1 and TNFR2 (FIG. 3B).

FIG. 8F notably and unexpected demonstrates that 82% of patients responded to anti-TNF and anti-IL-33. Additionally, it was also unexpectedly shown that 100% of patients respond to anti-TNFR2 and anti-IL-33. Therefore, applicants have shown that targeting TNFR2 and IL-33 is superior and advantageous compared to using anti-TNF and anti-IL-33. This could not have been predicted and was unexpected. IL-33 stimulates TNF production by classically activated macrophages and mast cells recruited during fibrosis. Elevated local levels of TNF lead to the synthesis of more IL-33 by palmar fibroblasts as they differentiate into myofibroblasts. This in turn promotes further TNF production, creating a positive feedback loop and a chronic fibrotic response. Furthermore, IL-33 enhances the expression of its ST2 receptor on myofibroblasts, thereby inducing a positive autocrine feedback loop (FIG. 10).

Example 2

Periodic administration of a therapeutically effective amount of an IL-33 antagonist to a patient suffering from Dupuytren's disease successfully treats the patient.

Example 3

Periodic administration of a therapeutically effective amount of an IL-33 antagonist to a patient suffering from frozen shoulder successfully treats the patient.

Example 4

Periodic administration of a therapeutically effective amount of an IL-33 antagonist to a patient suffering from periarticular fibrosis successfully treats the patient.

Example 5

Periodic administration of a therapeutically effective amount of an IL-33 antagonist to a patient suffering from keloid or hypertrophic scars successfully treats the patient.

Example 6

Periodic administration of a therapeutically effective amount of an IL-33 antagonist to a patient suffering from endometriosis successfully treats the patient.

Example 7

Periodic administration of a therapeutically effective amount of an IL-33 antagonist to a patient suffering from abdominal adhesions successfully treats the patient.

Example 8

Periodic administration of a therapeutically effective amount of an IL-33 antagonist to a patient suffering from Ledderhose disease successfully treats the patient.

Example 9

Periodic administration of a therapeutically effective amount of an IL-33 antagonist to a patient suffering from Peyronie's disease successfully treats the patient.

Example 10

Periodic administration of a therapeutically effective amount of an IL-33 antagonist to a patient suffering from peritendinous adhesions successfully treats the patient.

Example 11

Periodic administration of a therapeutically effective amount of an IL-33 antagonist to a patient suffering from periarticular fibrosis successfully treats the patient.

Example 12

Co-administration of a therapeutically effective amount of an IL-33 antagonist and a therapeutically effective amount of a TNF-α antagonist to a patient suffering from Dupuytren's disease successfully treats the patient.

Example 13

Add-On Therapy for Treating Dupuytren's Disease

Periodic administration of an IL-33 antagonist as an add-on therapy for a human patient afflicted with Dupuytren's disease who is already receiving an TNF-α antagonist provides a clinically meaningful advantage and is more effective (provides at least an additive effect or more than an additive effect) in treating the patient than when the TNF-α antagonist is administered alone (at the same dose).

Periodic administration of a TNF-α antagonist as an add-on therapy for a human patient afflicted with Dupuytren's disease who is already receiving an IL-33 antagonist provides a clinically meaningful advantage and is more effective (provides at least an additive effect or more than an additive effect) in treating the patient than when the IL-33 antagonist is administered alone (at the same dose).

The add-on therapies also provides efficacy (provides at least an additive effect or more than an additive effect) in treating the patient without undue adverse side effects or affecting the safety of the treatment:
1. The add-on therapy is effective (provides at least an additive effect or more than an additive effect) in improving nodule size and vascularity.
2. The add-on therapy is effective (provides at least an additive effect or more than an additive effect) in improving grip strength and range of motion of the affected digit.

Example 14

Combination Therapy for Treating Dupuytren's Disease

Disclosed herein is the use of an IL-33 antagonist in addition to or in combination with a TNF-α antagonist for the treatment of Dupuytren's disease.

Periodic administration of a IL-33 antagonist in combination with a TNF-α antagonist to a human patient afflicted with Dupuytren's disease provides increased efficacy (provides at least an additive effect or more than an additive effect) in treating the patient than when a TNF-α antagonist is administered alone or when an IL-33 antagonist is administered alone (at the same dose). The combination therapy also provides efficacy (provides at least an additive effect or more than an additive effect) in treating the patient without undue adverse side effects or affecting the safety of the treatment.

The combination therapy provides a clinically meaningful advantage and is more effective (provides at least an additive effect or more than an additive effect) in treating the patient than when the IL-33 antagonist or a TNF-α antagonist is administered alone (at the same dose) in the following manner:
1. The combination therapy is effective (provides at least an additive effect or more than an additive effect) in improving nodule size and vascularity.
2. The combination therapy is effective (provides at least an additive effect or more than an additive effect) in improving grip strength and range of motion of the affected digit.
3. The combination therapy reduces the frequency of injections needed to treat Dupuytren's disease.
4. The combination therapy is effective in (provides at least an additive effect or more than an additive effect) treating a greater percentage of patients than either the IL-33 antagonist alone or the TNF-α antagonist alone.
5. The combination therapy delays the progression of early disease stage.

Example 15

Inhibition of Expression of TNFR2, ST2 and Most Effectively TNFR2+ST2 Down Regulates Myofibroblast Phenotype (FIGS. 8G-8I)

Methods for siRNA.

Cultured myofibroblasts from patients with Dupuytren's disease were used up to passage 2. 400,000 cells were mixed with 100 µl of Nucleofector Kit for Human Dermal Fibroblast transfection reagent (VPD-1001, Lonza) and 60 nM silencer select siRNA (Applied Biosystem), then electroporated using the AMAXA nucleofection 2b Device (Lonza) to transfect the siRNA probes. Inventoried silencer-select reagents and respective non-targeting negative controls were used for TNFR1 (4390824s, siRNA ID s14265), TNFR2 (439420, siRNA ID s14270), IL1RL1 (439420, s17532, Applied Biosystems).

```
TNFR2 sense 5' to 3:
                                    (SEQ ID NO: 1)
GCCUUGGGUCUACUAAUAATT.

TNFR1 sense 5' to 3:
                                    (SEQ ID NO: 2)
CGGUGACUGUCCCAACUUUTT.

IL1RL1 sense 5' to 3:
                                    (SEQ ID NO: 3)
GUUACACCGUGGAUUGGUATT.
```

Negative control siRNAs 1(4390843) and 2 (4390846) (Applied Biosystems) were used with sequences that do not target any gene product and provide a baseline to compare siRNA-treated samples. Cells were immediately transferred to a 6-well plate with 2 ml OptiMEM (31985062, Life Technologies) without serum, pre-warmed to 37° C. in an incubator with 5% CO2. After 16 h the transfection medium was washed three times with Phosphate Buffered Saline, before being replaced by DMEM with 10% FBS and 1% penicillin/streptomycin and incubated for another 32 h in a 37° C. incubator with 5% CO2. RT-PCR analysis was used to quantify knockdown of gene as previously described.

Discussion and Results:

TNFR1 expression is effectively down regulated by siRNA knockdown of TNFR1, TNFR1+TNFR2 or TNFR1+ST2 knockdown. TNFR2 expression is reduced by siRNA knockdown of TNFR2, TNFR1+TNFR2 or TNFR2+ST2 knockdown. ST2 expression is reduced by siRNA knockdown of ST2, TNFR1+ST2 or TNFR2+ST2 knockdown. Myofibroblast phenotype is down regulated as evidenced by α-SMA expression by siRNA knock down of TNFR2 (but not TNFR1) or ST2 and most effectively by siRNA knockdown of TNFR2+ST2 at mRNA and protein levels. Expression of COL1A1 mRNA, another marker of the myofibroblast phenotype, is reduced by siRNA knockdown of TNFR2 (but not TNFR1), ST2 or TNFR2+ST2 (FIGS. 8G-8I).

Example 16

Co-administration of a therapeutically effective amount of an IL-33 antagonist and a therapeutically effective amount of a TNFR2 antagonist to a patient suffering from Dupuytren's disease successfully treats the patient.

Example 17

Add-On Therapy for Treating Dupuytren's Disease

Periodic administration of an IL-33 antagonist as an add-on therapy for a human patient afflicted with Dupuytren's disease who is already receiving an TNFR2 antagonist provides a clinically meaningful advantage and is more effective (provides at least an additive effect or more than an additive effect) in treating the patient than when the TNFR2 antagonist is administered alone (at the same dose).

Periodic administration of a TNFR2 antagonist as an add-on therapy for a human patient afflicted with Dupuytren's disease who is already receiving an IL-33 antagonist provides a clinically meaningful advantage and is more effective (provides at least an additive effect or more than an additive effect) in treating the patient than when the IL-33 antagonist is administered alone (at the same dose).

The add-on therapies also provides efficacy (provides at least an additive effect or more than an additive effect) in treating the patient without undue adverse side effects or affecting the safety of the treatment:

1. The add-on therapy is effective (provides at least an additive effect or more than an additive effect) in improving nodule size and vascularity.
2. The add-on therapy is effective (provides at least an additive effect or more than an additive effect) in improving grip strength and range of motion of the affected digit.

Example 18

Combination Therapy for Treating Dupuytren's Disease

Disclosed herein is the use of an IL-33 antagonist in addition to or in combination with a TNFR2 antagonist for the treatment of Dupuytren's disease.

Periodic administration of a IL-33 antagonist in combination with a TNFR2 antagonist to a human patient afflicted with Dupuytren's disease provides increased efficacy (provides at least an additive effect or more than an additive effect) in treating the patient than when a TNFR2 antagonist is administered alone or when an IL-33 antagonist is administered alone (at the same dose). The combination therapy also provides efficacy (provides at least an additive effect or more than an additive effect) in treating the patient without undue adverse side effects or affecting the safety of the treatment.

The combination therapy provides a clinically meaningful advantage and is more effective (provides at least an additive effect or more than an additive effect) in treating the patient than when the IL-33 antagonist or a TNFR2 antagonist is administered alone (at the same dose) in the following manner:

1. The combination therapy is effective (provides at least an additive effect or more than an additive effect) in improving nodule size and vascularity.
2. The combination therapy is effective (provides at least an additive effect or more than an additive effect) in improving grip strength and range of motion of the affected digit.
3. The combination therapy reduces the frequency of injections needed to treat Dupuytren's disease.
4. The combination therapy is effective in (provides at least an additive effect or more than an additive effect) treating a greater percentage of patients than either the IL-33 antagonist alone or the TNFR2 antagonist alone.
5. The combination therapy delays the progression of early disease stage.

REFERENCES

Barbie, D. A. et al. Systematic RNA interference reveals that oncogenic KRAS-driven cancers require TBK1. Nature 462, 108-112 (2009)

Beaudreuil J (2012) La maladie de Dupuytren en 2012. Revue du Rhumatisme Monographies 79, 126-132.

Betz N et al. Radiotherapy in early-stage Dupuytren's contracture. Long-term results after 13 years. Strahlenther Onkol. 2010 February; 186(2):82-90.

Bischoff S. C. (2007). Role of mast cells in allergic and non-allergic immune responses: comparison of human and murine data. Nat. Rev. Immunol. 7, 93-104.

Brod et al. (2000) Annals. of Neurology, 47:127-131.

Bulstrode N W et al. The complications of Dupuytren's contracture surgery. J. Hand Surg. [Am]. 2005 September; 30(5):1021-5.

Chen N C, A systematic review of outcomes of fasciotomy, aponeurotomy, and collagenase treatments for Dupuytren's contracture. Hand (N Y). 2011 September; 6(3): 250-255.

Chiu, Ya-Lin and Rana, Tariq M. siRNA function in RNAi: A chemical modification analysis. RNA (2003), 9:1034-1048.

Crean S M et al. The efficacy and safety of fasciectomy and fasciotomy for Dupuytren's contracture in European patients: a structured review of published studies. J. Hand Surg. Eur. Vol. 2011 June; 36(5):396-407.

Dar, S. A. et al. siRNAmod: A database of experimentally validated chemically modified siRNAs. Sci. Rep. 6, 20031; doi: 10.1038/srep20031 (2016).

Davis et al., Gaps in exposure to essential competencies in hand surgery fellowship training: a national survey of program directors. Hand (N Y). 2013 March; 8(1): 1-11.

Deleavey, Glen F. and Damha, Masad J. Designing Chemically Modified Oligonucleotides for Targeted Gene Silencing, Chemistry & Biology, Volume 19, Issue 8, 24 Aug. 2012, Pages 937-954

National Institute for Health and Clinical Excellence (NICE), Radiation therapy for early Dupuytren's disease, NICE interventional procedure guidance 368 issued November 2010.

FDA 2005. Draft Guidance for Industry—Systemic Lupus Erythematosus—Developing Drugs for Treatment.

Gaglione, M. & Messere, A. Recent progress in chemically modified siRNAs. Mini reviews in medicinal chemistry 10, 578-595 (2010).

Gailit J et al. The differentiation and function of myofibroblasts is regulated by mast cell mediators. J. Invest. Dermatol. 2001 November; 117(5):1113-9.

Hindocha S et al. "Epidemiological Evaluation of Dupuytren's Disease Incidence and Prevalence Rates in Relation to Etiology." Hand (N Y). 2009 September; 4(3): 256-269.

Lagana, A et al. Computational Design of Artificial RNA Molecules for Gene Regulation. Methods Mol. Biol. 2015; 1269: 393-412.

Langer-Gould et al. (2005) New England Journal of Medicine, 353:369-379.

Luo, J. et al. A genome-wide RNAi screen identifies multiple synthetic lethal interactions with the Ras oncogene. Cell 137, 835-848 (2009)

Hughes T B et al. Dupuytren's Disease. J. Hand Surg. Am. 2003; 3:27-40.

Hurst et al. "Injectable Collagenase Clostridium Histolyticum for Dupuytren's Contracture" N ENGL J MED 361; 10 Sep. 3, 2009.

Hinz B, Alpha-Smooth Muscle Actin Expression Upregulates Fibroblast Contractile Activity. Mol. Biol. Cell. 2001 September; 12(9): 2730-2741.

Kanasty, R. et al. Delivery materials for siRNA therapeutics. Nature Mater. 12, 967-977 (2013).

Kakkar T, Lee R T, The IL-33/ST2 pathway: therapeutic target and novel biomarker. Nat. Rev. Drug Discov. 2008 October; 7(10):827-40.

Kleinschmidt-DeMasters et al. (2005) New England Journal of Medicine, 353:369-379.

Ketchum L D, Donahue T K, The injection of nodules of Dupuytren's disease with triamcinolone acetonide. J. Hand Surg. Am. 2000 November; 25(6):1157-62.

Kobori A et al. (2010) Interleukin-33 expression is specifically enhanced in inflamed mucosa of ulcerative colitis. J. Gastroenterol.

Kontermann R E, "Dual targeting strategies with bispecific antibodies" mAbs 4:2, 182-197; March/April 2012.

Kunisch E et al. IL-33 regulates TNF-α dependent effects in synovial fibroblasts. Int. J. Mol. Med. 2012 April; 29(4): 530-40.

Larson D et al. Clinical effectiveness of post-operative splinting after surgical release of Dupuytren's contracture: a systematic review. BMC Musculoskeletal Disorders 2008, 9:104.

Moulin D. (2007) Interleukin (IL)-33 induces the release of pro-inflammatory mediators by mast cells. Cytokine 40, 216-225.

Paddison P J, et al. Short hairpin RNAs (shRNAs) induce sequence-specific silencing in mammalian cells. Genes Dev. 2002; 16:948-958.

Paladini et al. "Mutations in the Catalytic Domain of Human Matrix Metalloproteinase-1 (MMP-1) That Allow for Regulated Activity through the Use of Ca2+" THE JOURNAL OF BIOLOGICAL CHEMISTRY VOL. 288, NO. 09. pp. 6629-6639, Mar. 1, 2013.

Palmer G, Gabay C, "Interleukin-33 biology with potential insights into human diseases." Nat. Rev. Rheumatol. 7, 321-329 (2011)

Pastorelli L. et al. (2010) Epithelial-derived IL-33 and its receptor ST2 are dysregulated in ulcerative colitis and in experimental Th1/Th2 driven enteritis. Proc. Natl. Acad. Sci. USA 107: 8017-8022.

Peimer C A at al., Dupuytren contracture recurrence following treatment with collagenase clostridium histolyticum (CORDLESS study): 3-year data. J. Hand Surg. Am. 2013 January; 38(1):12-22.

Pohl S, et al. (2002) Prophylactic radiotherapy in Dupuytren's contracture: three years outcome. International Journal of Radiation Oncology Biology Physics 54: 23.

Rankin A L et al. IL-33 induces IL-13-dependent cutaneous fibrosis. J. Immunol. 2010 Feb. 1; 184(3):1526-35.

Rayan G. M. (2007). Dupuytren disease: anatomy, pathology, presentation, and treatment. J. Bone Joint Surg. Am. 89, 189-198.

Rombouts, J. Hand Surg. Am, 14, 644-652, 1989.

Schiering C et al. The alarmin IL-33 promotes regulatory T-cell function in the intestine. Nature. 2014 Sep. 25; 513 (7519):564-8.

Silva, J. M. et al. Profiling essential genes in human mammary cells by multiplex RNAi screening. Science 319, 617-620 (2008)

Rao, D. D. et al. Enhanced target gene knockdown by a bifunctional shRNA: a novel approach of RNA interference. Cancer Gene Ther. 17:780-791 (2010).

Rudick, R. (1999) "Disease-Modifying Drugs for Relapsing-Remitting Multiple Sclerosis and Future Directions for Multiple Sclerosis Therapeutics", Neurotherpatueics. 56:1079-84.

Schmitz J et al. IL-33, an interleukin-1-like cytokine that signals via the IL-1 receptor-related protein ST2 and induces T helper type 2-associated cytokines. Immunity. 2005 November; 23(5):479-90.

Seegenschmiedt M et al. "Radiotherapy for Non-Malignant Disorders" Springer (Berlin, N.Y., 2008).

Sponheim J et al. Inflammatory bowel disease-associated interleukin-33 is preferentially expressed in ulceration-associated myofibroblasts. Am. J. Pathol. 2010; 177:2804-2815.

Summary basis of approval XIAFLEX-EU: Available at www.ema.europa.eu/docs/en_GB/document_library/ EPAR_-Product_Information/human/002048/ WC500103373.pdf Taylor M C (2005) Interviewing. In Qualitative Research in Healthcare (Holloway I ed). Open University Press, Berkshire, pp. 39-53.

Chang K, et al. Tools for studying and using small RNAs: from pathways to functions to therapies. Nature Reviews, Genetics Sep. 18, 2014.

Tracy et al. "Tumor necrosis factor antagonist mechanisms of action: A comprehensive review" Pharmacology & Therapeutics 117 (2008) 244-279.

Ullah A S et al. (2009) Does a 'firebreak' full-thickness skin graft prevent recurrence after surgery for Dupuytren's contracture?: a prospective, randomised trial. J. Bone Joint Surg. Br. 91: 374-378.

van Rijssen A L et al. Five-year results of a randomized clinical trial on treatment in Dupuytren's disease: percutaneous needle fasciotomy versus limited fasciectomy. Plast. Reconstr. Surg. 2012 February; 129(2):469-77.

Verjee at al. "Unraveling the signaling pathways promoting fibrosis in Dupuytren's disease reveals TNF as a therapeutic target" PNAS vol. 110 no. 10 published Feb. 19, 2013.

Vollmer et al. (2008) "Pridopidine after induction therapy with mitoxantrone in relapsing multiple sclerosis" Multiple Sclerosis, //00:1-8.

Xu D et al. IL-33 exacerbates antigen-induced arthritis by activating mast cells. PNAS, Aug. 5, 2008, vol. 105, no. 31, 10913-10918.

What is claimed is:

1. A method of treating a patient suffering from frozen shoulder (adhesive capsulitis) or periarticular fibrosis which comprises administering to the patient locally at the site of the frozen shoulder (adhesive capsulitis) or periarticular fibrosis, an IL-33 antagonist which is an antibody that specifically binds to, and inhibits activation of, an IL-33 receptor or a binding fragment of such an antibody that specifically binds to and inhibits activation of an IL-33 receptor in an amount effective to downregulate expression of alpha-SMA, ST2 and COL1A1 in the patient's myofibroblasts so as to thereby treat the patient.

2. The method of claim 1 wherein the IL-33 antagonist is injected into a site of maximal cellularity or maximal inflammation.

3. The method of claim 1 wherein the effective amount of the IL-33 antagonist is an amount between 0.1 mg and 500 mg.

4. The method of claim 1, which further comprises co-administering a TNF-α antagonist.

5. The method of claim 4, wherein the amount of the TNF-α antagonist is between 5 mg and 300 mg.

6. The method of claim 4, wherein the TNF-α antagonist is one or more of infliximab, adalimumab, certolizumab pegol, golimumab or etanercept.

7. The method of claim 6, wherein the TNF-α antagonist is golimumab and the amount of golimumab administered is between 1 mg and 90 mg.

8. The method of claim 6, wherein the TNF-α antagonist is adalimumab and the amount of adalimumab administered is between 5 mg and 100 mg.

9. The method of claim 6, wherein the TNF-α antagonist is certolizumab pegol and the amount of certolizumab pegol administered is between 50 mg and 200 mg.

10. The method of claim 6, wherein the TNF-α antagonist is infliximab and the amount of infliximab administered is between 50 mg and 300 mg.

11. The method of claim 6, wherein the TNF-α antagonist is etanercept and the amount of etanercept administered is between 5 mg and 50 mg.

12. The method of claim 4, wherein the TNF-α antagonist is a TNF receptor 2 (TNFR2) antagonist.

13. The method of claim 1, wherein the antibody is a chimeric antibody, a humanized antibody, or a human antibody.

14. The method of claim 1, wherein the patient is suffering from frozen shoulder (adhesive capsulitis).

15. The method of claim 1, wherein the patient is suffering from periarticular fibrosis.

16. The method of claim 1, wherein the IL-33 antagonist is administered daily, weekly, monthly, every three months, every 6 months, or every 12 months.

17. A method of treating a patient suffering from frozen shoulder (adhesive capsulitis) or periarticular fibrosis which comprises co-administering to the patient locally at the site of the frozen shoulder (adhesive capsulitis) or periarticular fibrosis, an IL-33 antagonist which is (a) an antibody that specifically binds to, and inhibits activation of, an IL-33 receptor or (b) a binding fragment of such an antibody that specifically binds to and inhibits activation of an IL-33 receptor and (c) a GM-CSF antagonist, in amounts effective to downregulate expression of alpha-SMA, ST2 and COL1A1 in the patient's myofibroblasts so as to thereby treat the patient.

18. A method of treating a patient suffering from frozen shoulder (adhesive capsulitis) or periarticular fibrosis which comprises co-administering to the patient locally at the site of the frozen shoulder (adhesive capsulitis) or periarticular fibrosis, (a) an IL-33 antagonist which is an antibody that specifically binds to, and inhibits activation of, an IL-33 receptor or (b) a binding fragment of such an antibody that specifically binds to and inhibits activation of an IL-33 receptor and (c) one or more of an IL-17 antagonist, an IL-21 antagonist, or an IL-23 antagonist, in amounts effective to downregulate expression of alpha-SMA, ST2 and COL1A1 in the patient's myofibroblasts so as to thereby treat the patient.

\* \* \* \* \*